Figure 1:
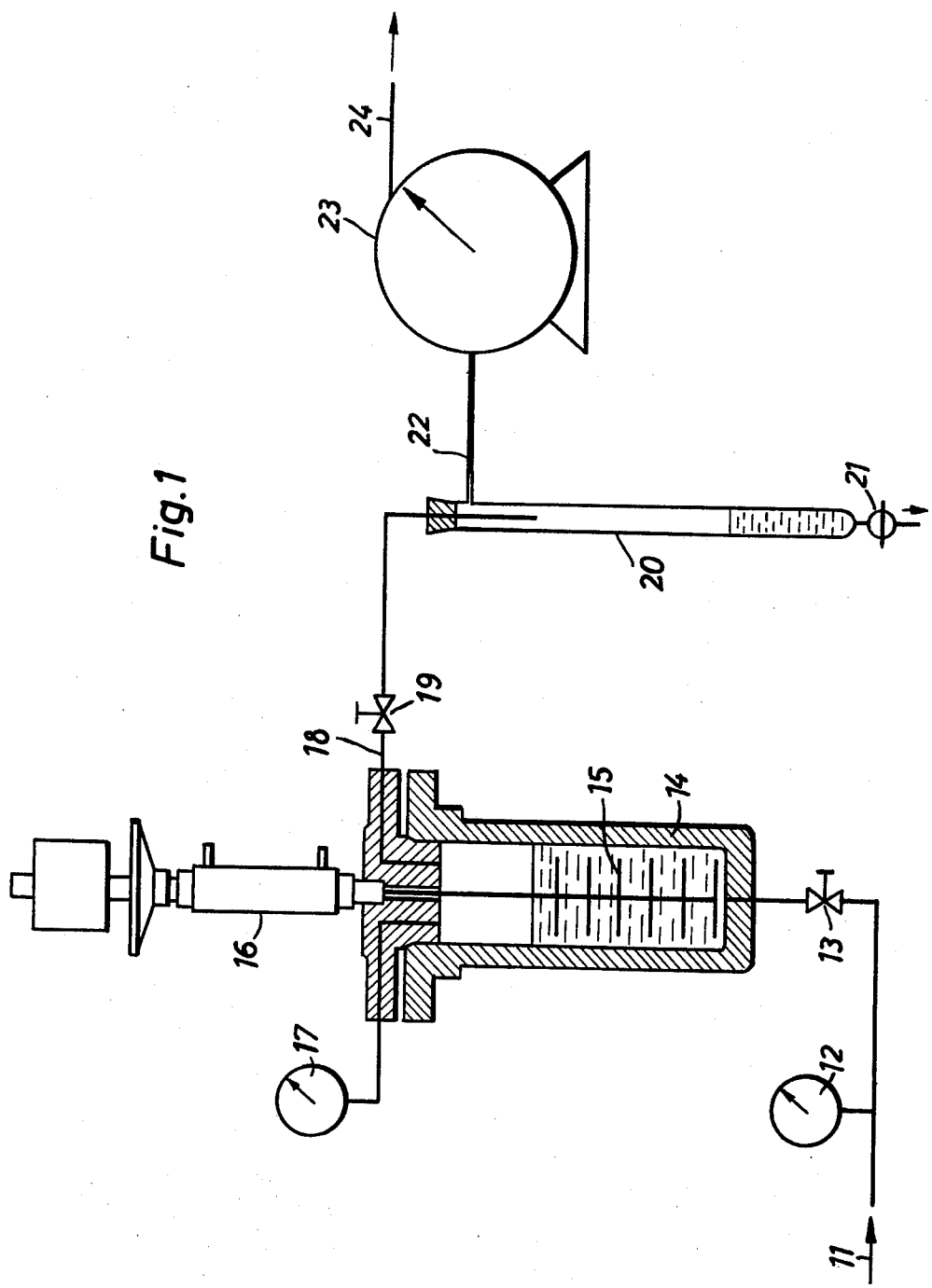

United States Patent [19]
Zosel

[11] 3,969,196
[45] July 13, 1976

[54] PROCESS FOR THE SEPARATION OF MIXTURES OF SUBSTANCES

[75] Inventor: Kurt Zosel, Oberhausen-Rhineland, Germany

[73] Assignee: Studiengesellschaft Kohle m.b.H., Mulheim (Ruhr), Germany

[22] Filed: Dec. 9, 1969

[21] Appl. No.: 880,475

Related U.S. Application Data
[63] Continuation of Ser. No. 359,680, April 14, 1964, abandoned.

[30] Foreign Application Priority Data

| Apr. 16, 1963 | Austria | 3085/63 |
| July 26, 1963 | Austria | 6005/63 |
| July 26, 1963 | Austria | 6006/63 |
| Aug. 7, 1963 | Austria | 6366/63 |
| Nov. 20, 1963 | Austria | 9310/63 |
| Dec. 18, 1963 | Austria | 10203/63 |

[52] U.S. Cl. ............ 203/49; 208/308; 208/337
[51] Int. Cl.² ............ B01D 3/24; C10G 21/14
[58] Field of Search ............ 203/49; 62/16; 208/356

[56] References Cited
UNITED STATES PATENTS

| 2,166,160 | 7/1939 | King | 208/313 |
| 2,242,173 | 5/1941 | Buckley | 62/16 |
| 2,391,576 | 12/1945 | Katz et al. | 62/16 |
| 2,391,607 | 12/1945 | Whaley | 208/356 |
| 2,596,785 | 5/1952 | Nelly, Jr. et al. | 62/28 X |
| 2,916,887 | 12/1959 | Brooke | 62/28 X |

*Primary Examiner*—Norman Yudkoff
*Assistant Examiner*—J. Sofer
*Attorney, Agent, or Firm*—Burgess, Dinklage & Sprung

[57] ABSTRACT

The process of separating a mixture which is in liquid state or solid state or liquid and solid state and contains at least one compound containing an organic group, which comprises
a. contacting said mixture with a gas maintained under supercritical conditions of temperature and pressure such that the gas will take up at least a portion of said mixture in a quantity varying inversely with said temperature, and effecting said contacting in a manner so that this occurs, and so that there is a substantial gas component that is identifiable as gas phase,
b. separating the gas in the form of said identifiable gas phase loaded with the compound taken up during said contacting from any of the mixture not taken up by the gas while still maintaining supercritical conditions as aforesaid,
c. thereafter separating the compound from the gas.

24 Claims, 6 Drawing Figures

PROCESS FOR THE SEPARATION OF MIXTURES OF SUBSTANCES

This application is a continuation of application Ser. No. 359,680, filed Apr. 14, 1964 now abandoned.

This invention relates to a process for the separation of mixtures of substances.

Distillation and solvent extraction are the two most important processes for the separation of mixtures of substances. Distillation has the known disadvantage that the mixtures to be separated must be heated at temperatures which are the higher the lower the vapor pressure of the substances to be separated. Limits are set to distillation where the substances are no longer thermally stable. Use of vacuum widens the field of application of this separation process, but only by an additional boiling interval of about 100° to 150°C. The well-known solvent extraction process is only of limited applicability because the selection of suitable solvents frequently offers great difficulties or because suitable solvents do not exist at all. On the other hand, limits are placed on this process where the solubility characteristics of the components of the mixture to be separated are so similar that efficient separation is no longer obtained. The effect of these two prior art processes is not equivalent. Distillation effects separation of the substance mixtures according to boiling characteristics while solvent extraction gives separation of the substances according to the type of the class of material but not according to the boiling characteristics as does distillation.

It is an object of this invention to provide a new separation process which constitutes a new efficient means to separate mixtures of substances in a simple manner. The new process effects preferential separation according to boiling characteristics without the necessity of effecting distillation in the customary sense with evaporation of the mixture being separated. Deviations from this general rule with respect to the separation effect of the new process may occur in accordance with the nature of the process. The separation process of this invention is extremely simple in operation and permits the separation of large quantities of materials thereby creating new possibilities of separating mixtures of materials or purifying reaction products, especially on a commercial scale.

The invention is based on two fundamental observations. Firstly, it has been found that supercritical gaseous phases are capable on principle of taking up the classes of compounds described hereafter under supercritical conditions, the amount of material being taken up by the supercritical gas being by many times greater than would have been expected from the vapor pressure of these compounds at the temperature of the treatment. Thus, supercritical gases under the conditions used in accordance with the invention constitute media which are capable of taking up large amounts of materials without, however, being conventional solvents from which they differ inter alia in that they are gases rather than liquids.

Secondly, within those classes of materials which on principle are capable of being taken up in the supercritical gas phase, the "transferability" into the supercritical gas is dependent upon the specific constitution of the compound. The tendency to pass into the supercritical gas phase is, therefore, not the same for the compounds. The higher the extent to which a compound is capable of being taken up in the supercritical gas, the more rapidly this compound will pass over into the supercritical gas phase under otherwise comparable reaction conditions or the higher will be the portion which is taken up by a given amount of the supercritical gas phase. Similar considerations apply to the portion of the particular compound which is taken up by a given amount of the supercritical gas per unit time. The separation process of the invention is operative on the basis of these and several other principles described hereafter.

Accordingly, it is an object of this invention to provide a proces for the separation of mixtures of substances which are liquid and/or solid under the process conditions and which contain organic compounds and/or organic radicals, the process comprising contacting said mixture with a gas maintained under supercritical conditions of temperatures and pressure thereby taking up in said supercritical gas phase at least part of said organic compounds and/or compounds containing organic groups, separating, if necessary or desired, the loaded gas under supercritical conditions from that portion of the mixture which has not been taken up, and subsequently recovering from the supercritical gas phase the compounds taken up therein. If, in the treatment of the substance mixture to be separated, the latter is completely taken up by the supercritical gas phase, then the different components of the compounds taken up are separately recovered from the supercritical gas phase. If only part of the mixture of substances is taken up by the supercritical gas phase, then the compounds taken up by the gas phase can be recovered as a whole or in the form of separate components. It is preferred to operate as follows: All of the substance mixture to be separated or components thereof are taken up by a stream of the supercritical gas contacted with the mixture. The components of the mixture are recovered from this supercritical gas stream which is preferably passed continuously through the mixture of substances to be separated, the recovery being preferably effected by raising the temperature and/or by lowering the pressure of the loaded gas stream.

It has already become known that certain gas phases maintained under supercritical conditions, e.g. supercritical ethylene, are capable of taking up larger amounts of certain solids. Particularly careful studies were directed to the ternary system comprising supercritical ethylene, naphthalene and hexachloroethane. It has been found in these studies that ethylene takes up these two solids in larger amounts than corresponds to the vapor pressures of the compounds at the treating temperature. In connection with earlier studies published in literature, the question also arose whether specific solids mixtures can be separated by means of a supercritical gas phase under specific conditions. Published reports on these studies show that they did not lead to satisfactory results. It has now been found in absolute contrast to the prior art results that the supercritical gas phase constitutes an outstanding means for separating substances not only under very specific conditions but that there is involved a wide operating principle of general applicability permitting the separation of liquid and/or solid mixtures of substances under the process conditions.

In studying the degree to which chemical compounds can be taken up in supercritical gases, it was found that especially organic compounds are subject to this effect. However, this phenomenon of the passage of unexpectedly large amounts of a compound into the supercritical gas phase is not restricted to purely organic compounds. Compounds of mixed structure containing other structural members in addition to organic groups can, on principle, be taken up by the supercritical gas phase. Examples of such mixed compounds include organometallic compounds such as metal alkyls, metal alcoholates, silicones, boroalkyls, but also compounds of a completely different type such as organic esters of inorganic acids, e.g. esters of sulfuric acid, phosphoric acid, and others. Organosilicon compounds are another example.

By selecting suitable conditions for the treatment with a supercritical gas phase, these mixed compounds can also be taken up in the supercritical phase as a rule. Thus, the invention comprises not only the separation of mixtures containing purely organic compounds but also that of mixtures of this kind having a content of compounds containing organic groups. If there are doubts in individual cases, it is rapidly ascertained by a simple test whether or not the particular mixture of substances contains components which are capable of being taken up by the supercritical gas, it being merely necessary to treat a small sample of this mixture with a supercritical gas phase under the conditions of the invention. Examination of this supercritical gas phase will show whether or not components of the mixture to be separated have been taken up. This transferability of at least part of the mixture to be separated into the supercritical gas phase is the condition for the applicability of the new separation process.

As was mentioned above, the transferability into the paticular supercritical gas phase under the particular process conditions is variable among the compounds which on principle are amenable to the new separation and depends on the constitution of the particular compounds. Without intending to give a detailed explanation of this phenomenon, it is believed that solvation of the compounds of the liquid or solid mixture of substances with the separating gas and the characteristics of the materials thus solvated are among the factors which are determinative for the transition into the supercritical gas phase. It appeared that especially organic groups are amenable to such solvation with the gases used in accordance with the invention, this being an explanation of the selection of these compounds for use in the process of this invention. Solvatability of the particular compound and the characteristics of the solvated products are, however, definitely dependent inter alia upon the specific constitution of the particular compound. It can be assumed that these differences are among the factors which are responsible for the fact that transferability into the supercritical gas phase of different compounds under given conditions is different. Thus, for example, some interrelationship has been found to exist between transferability or absorbability and volatility. The rate at which a compound is taken up by a supercritical gas and the proportion of the compound taken up increase as volatility of said compound increases. On the other hand, for example, introduction of hetero atoms such as nitrogen or oxygen into pure hydrocarbon compounds may influence absorbability of these modified compounds in the supercritical gas. Finally, some interrelationship has been found to exist between the constitution of the compounds to be taken up and that of the supercritical gas. All of these effects may be relied on within the scope of the process of the invention and utilized to advantage. Simple examples hereof are as follows:

When applying the process of the invention to a mixture of materials which, in addition to compounds which are capable of being taken up in the supercritical gas, comprises compounds which do not exhibit this capability, separation can be effected by causing the one part to be taken up by the supercritical gas phase and recovering it therefrom. If, on the other hand, the treatment is applied to a mixture which contains several compounds absorbable in the supercritical gas phase or which exclusively consists of compounds of this kind which, however, are different among one another with respect to the degree they are capable of being taken up by the supercritical gas, then it can be achieved by suitable selection of the conditions used in effecting the treatment with the supercritical gas that those compounds which are most readily taken up by the supercritical gas pass preferentially or exclusively into said phase while those compounds which are less readily taken up remain. As a rule, in case of compounds of different volatilities, those being most volatile will invariably pass preferentially into the supercritical gas phase. In this manner, separation of the mixture of substances is possible. It is also possible in case of mixtures of a more complex nature to isolate fractions of compounds of different volatilities. Finally, it will be described hereafter that it is also possible to cause a mixture to pass into the supercritical gas phase and thereafter effect the separation from this gas phase by recovering the individual compounds or different fractions of several compounds separately from the supercritical gas phase.

As a general rule, the separation of mixtures of substances by means of supercritical gas phases in accordance with the invention is based on the phenomenon described above, i.e. that the individual compounds of of the mixture to be separated are different with respect to the degree to which they are "absorbable" by the particular supercritical gas. There is a great variety of possibilities within the scope of the process of the invention to utilize this phenomenon for achieving the separation desired.

If that combination of process conditions which is most favorable for the particular separation within the scope of the process of the invention is not known from the outset, it can be ascertained by a few preliminary experiments. It is just this possibility of adapting the reaction conditions of the invention to the particular separation problem to be solved which is an advantage of the process of the invention because it becomes possible in this manner to effect in a simple manner separations which are otherwise difficult.

While it was mentioned above that there is some interrelationship between the nature of the compounds to be taken up and that of the supercritical gas, this interrelationship is of minor importance and becomes significant only in special cases. It has been found surprisingly that the nature of the gas phase, i.e. chemical constitution of the gas used in supercritical state, is of minor importance to the phenomenon of the taking-up of the compounds to be separated. Thus, it is possible but by no means necessary to use chemically related gases such as lower hydrocarbons for the separation of organic compounds. Transfer of organic compounds is achieved equally satisfactorily in purely inorganic gases such as $CO_2$. Thus, rules or principles which apply to conventional solution processes, especially those in the liquid phase, are not applicable in this case. Therefore, both organic and inorganic compounds may be used as the supercritical gas phase. In special cases, selection of a specific type of compound as supercritical gas may be desirable or necessary. Difficulties may be encountered in special cases to cause simple organic compounds or compounds containing organic groups to pass into the otherwise very efficient supercritical gas phases such as lower hydrocarbons. A typical example hereof are polyfunctional alcohols, even the lower members of which such as glycol, glycerol and related compounds offer difficulties in being transferred into gases such as, for example, supercritical ethane, ethylene or similar compounds. There must exist additional intermolecular forces resisting solvation by the molecules of the supercritical gas phase and detachment of solvated molecules from their association in the organic compound. Presumably the higher number of hydrocyl groups per molecule is playing a part in this connection, it having been found that comparable monofunctional alcohols are considerably more readily taken up by the supercritical hydrocarbon than are glycols or other polyfunctional alcohols. In these and similar cases, selection of particular gases has been found to be desirable, good results being obtained especially with ammonia. Probably polarity of the ammonia molecule exerts an additional effect and renders amenable to solvation and consequently isolation from the original lattic of molecules even those materials which resist corresponding treatment with less polar or non-polar supercritical gases. A comparable difficulty with respect to transfer into the supercritical gas is encountered if, for example, a conventional cutting oil emulsion which, as is known, is an emulsion of, for example, spindle oil in water is subjected to the treatment with supercritical hydrocarbon gases. Here again, it is difficult to cause portions of the organic phase of the aqueous emulsion phase to pass into the supercritical gas while nonemulsified spindle oil passes into the supercritical phase without any difficulty.

Apart from these special cases, the rule is applicable that any supercritical gas phase takes up more or less well the compounds to be separated under the specific conditions used in accordance with the invention. Of course, the requirement must be met by the gas selected that it does not react with the compounds being separated during separation but merely serves as a carrier gas for the components of the mixture. Selection of the gas to be used in each case is determined by the other reaction variables of the new process which are discussed hereafter.

It appeared in general that the quantity of material taken up in the supercritical gas becomes the greater the more the operating temperature approaches the critical temperature. Therefore, it is preferred in accordance with the invention to operate in a temperature range which is relatively close to and above the critical temperature of the gas used. For example, the treatment may be effected within a temperature range as much as 100°C. above the critical temperature, but a temperature range which is considerably closer to the critical temperature is preferred. For example, suitable is a range up to 50°C. above the critical temperature, it being particularly preferred to operate in the range up to about 20°C. above this critical temperature. The selection of the inert gas phases used in the process is explained by this fact. Preferred compounds are those, the critical temperatures of which range only slightly below the selected operating temperature thus making possible as close as possible an approximation of the operating temperature to the critical temperature of this gas phase. Actually, it is possible to operate within a very wide temperature range which substantially is determined more by constructional and economic considerations than by fundamental limits set by natural science. A suitable temperature range is, for example, from −100°C. to about +300°C., the narrower range between about 0°C. to about 200° C. appearing to be particularly convenient for commercial operation. Temperatures below −100°C. involve problems due to embrittlement of materials while a comparable problem is faced at excessively high temperatures, e.g. at temperatures in excess of 300°C. However, it is to be understood that, on principle, these higher temperatures are also usable when suitably selecting the gas phase.

Furthermore, the very general rule applies that the quantity of material taken up in the gas phase increases as the pressure used increases. The surprising increase in the amount of material in the supercritical gas phase begins approximately in the vicinity of critical pressure, the phenomenon of the sudden increase in the amount of compound taken up per unit quantity of the gas phase being also observed slightly below this pressure. On principle, operation under supercritical pressures is to be recommended. In this supercritical range of pressure, an upper limit on pressure does not appear to exist. Thus, here again, limitation is determined by engineering considerations rather than considerations of principle. Thus, operating pressures may, for example, be as high as several hundred atmospheres, e.g. 500 atmospheres, or higher, it being especially economic considerations in addition to problems in connection with materials of construction which deterine and, as the case may be, restrict this pressure range.

With consideration given to these two variables, it is seen that the quantity of the particular material taken up in the supercritical gas increases as the temperature approaches the critical temperature and as the operating pressure used increases. It is especially this combination of temperatures near the critical temperature and sufficiently elevated pressures, particularly supercritical pressures, which will be referred to as "supercritical conditions in accordance with the invention" in this specification. These process conditions and, among them, especially the critical temperature of the inert gas phase are largely determinative for the selection of the particular supercritical inert gas. Due to dependence of absorbability in the supercritical gas of the compounds to be separated on the critical temperature of the gas phase, the latter determines the approximate range of operating temperature so that the inert gas will be selected in dependence on the operating temperature desired and the critical gas temperature. Since it is preferred to carry out the process in the temperature range of about −100°C. to about +300°C. and particularly within the range of about 0° to about 200°C., there results a certain choice of carrier gases from the known critical temperatures of the compounds which are gaseous in this temperature range. Particularly preferred are hydrocarbon compounds, especially lower hydrocarbon compounds which may be saturated or unsaturated, especially olefinically unsaturated. Typical examples include, ethane, propane, butane, ethylene, propylene and corresponding halogenated hydrocarbon compounds such as chloro- or fluorohydrocarbons derived therefrom. Inorganic gases, especially carbon dioxide and ammonia, may also be used advantageously and, as mentioned above, the use of, for example, ammonia may be even mandatory. Other inorganic gases such as sulfur dioxide, hydrogen halide and the like can also be used on principle. In this case, however, considerable objections must be raised from the technological point of view because of aggressiveness of these compounds or the condition that the gas phases used must be inert to the substances being separated. Particularly important inert gases for effecting the separation in accordance with the invention are the lower hydrocarbons ethane, propane, ethylene and propene, i.e. compounds the critical temperature of which is within the range of room temperature or only moderately elevated temperatures. Mixtures of these compounds may also be used. Among inorganic gases, greater importance is supposed to be attributable to carbon dioxide, ammonia and $N_2O$ while corroding compounds such as HCl, $SO_2$, $H_2S$ and similar substances entail additional difficulties in practice. On principle, compounds having critical temperatures of from 0°C. to 200°C. are particularly preferred. The use of supercritical steam is not excluded but entails a number of particular difficulties due to the critical constants and the condition of the supercritical phase.

Based on this disclosure, a still more precise definition can also be given for the group of mixtures of materials which are particularly suitable for the performance of the process of the invention. The materials should be liquid or solid under the process conditions to ensure separation of a loaded supercritical gas phase from the starting mixture or formation of two phases in the separation process. Particularly preferred mixtures of substances are those which are liquid under the conditions of the process although solid mixtures of substances can also be separated advantageously by the new process.

While this definition, i.e. that the mixtures to be separated must be liquid or solid under the process conditions, is of general applicability, a peculiarity may become significant in special cases. It appeared that mixtures, especially liquid ones, may offer difficulties in the new separation process if vaporizability of at least part of these compounds under the operating conditions, especially at the operating temperature chosen, is high. Typical examples of compounds of this kind include relatively readily volatile hydrocarbon compounds, e.g. those boiling up to about 100°C. under normal conditions, when using ethylene or gases having a higher critical temperature. In case of these particularly readily volatile compounds, the inherent vapor pressure of these compounds at the operating temperature obviously becomes more significant than the processes which are otherwise responsible for the course of the process of the invention. The fact that obviously not only volatility, i.e. the boiling temperature of the particular compound, but also other quantities or factors among which is probably vaporizability play a decisive part for this interference effect, results from the fact that compounds having rather high boiling points may exhibit a similar interference if they have high vaporizability. On the other hand, this means that compounds may be used in the process of the invention even if they have a relatively low boiling point, but are difficult to evaporate. For example, in the treatment of hydrocarbon compounds with hydrocarbon separating gases such as ethylene or ethane, a useful rule has been found to be that, under normal conditions, the compounds to be separated should boil at least about 100°C above the critical temperature of the separating gas used. It may be recommendable in this connection to remove the disturbing, readily vaporizable or readily volatile compounds by conventional methods, e.g. by distillation, before treating mixtures of substances by the process of the invention.

In case of compounds which are not pronounced highpolymers, an upper limit of molecular size was not established up to the present unless additional phenomena such as the resistance described above of polyfunctional alcohols to being taken up in supercritical hydrocarbon compounds occur. Thus, paraffin oil boiling above 350°C. is taken up without any difficulty in supercritical ethylene or ethane. The same is true for silicone oil which has a substantially higher boiling point, its initial boiling point being in excess of 500°C. Similar observations were made in case of certain large molecules. In the field of natural substances, it was possible, for example, to drive over chlorophyll in the supercritical gas phase. The same is true for such a great mixed compound as a metal alkyl having three $C_{20}$ alkyl radicals. As was memtioned above, increasing molecular size or decreasing volatility is merely accompanied by a decrease in the quantity which is taken up per unit quantity of the supercritical gas under comparable process conditions. An expedient which may be relied upon in this case is adjustment of the process conditions, e.g. increase in pressure and/or increase in the amount of inert gas used. Solid materials such as naphthalene, phenanthrene or anthracene, and also natural substances such as camphor or chlorophyll can be taken up in the supercritical gas phase just as well as components or mixtures of substances which are liquid under the process conditions. Another interesting and important example is the treatment of petroleum or petroleum products by the new process. In this field, crude oil was successfully transferred into supercritical gas except for minor residues, it being remarkable that even those constituents of the crude oil which are normally solid pass over. Visually, a difference in the condition of the supercritical gas phase cannot be noticed in general.

The compounds which, in the new process, are taken up in the supercritical gas can be separated therefrom in a simple manner. This requires merely depressurization and/or an increase in temperature. When reducing the pressure below the critical limit, substantially the total amount of compounds taken up is precipitated. Economic considerations may determine the method of separation to be preferred. For example, if it is desirable for economic reasons to maintain the inert gas stream under constant or only slightly varying pressures during loading and release, heating of the loaded inert gas stream suffices to release increasingly large amounts of the compounds taken up with increasing temperatures of the stream. Very extensive separation of the compounds taken up is obtained if, for example, temperatures ranging more than 100°C. above the critical temperature are exceeded. When carrying out the process in practice where the supercritical inert gas stream is recycled between the loading and unloading or release steps, it is not even necessary to use these high temperatures in the unloading cycle since it is sufficient to separate part of the compounds taken up and to return into the loading cycle the inert gas stream which is again ready for being loaded. When effecting the unloading or release by depressurization, it may be preferred not to go below the critical pressure. This will always be the case if very extensive desolvation of the material taken up is to be prevented. Thus, it is preferred in these cases to effect adequate depressurization while maintaining the pressure above the critical pressure. Here again, it will not be disadvantageous in normal cases when operating with recycling of the inert gas stream that not all of the compounds taken up are released. If, however, total release is desired, the most convenient method of operation involves reduction in pressure to below the critical pressure of the inert gas phase used. Separation of the gas phase and the released solid or liquid phase is then effected easily by physical methods.

It is particularly important for the new process that transfer of the compounds into the supercritical gas phase and the reverse process, i.e. release of these compounds from the supercritical phase does not seem to involve a noticeable change in energy of the system. Thus, substantial cooling or heating effects do not occur during loading and release. This fact is not only important for the economy of the new process. It is also important because temperature largely influences the degree to which the supercritical gas phase can be loaded and troubles would have to be expected if these temperature effects would occur. It must be valued as a particularly fortunate fact that these troubles are not encountered.

As regards the release of the compounds taken up in the gas phase, a distinction is to be made between different cases. Most simple of these cases is that where a uniform compound was dissolved out of a mixture of substances by means of the supercritical inert gas stream so that said increase in temperature and/or depressurization results in a more or less pure separated product. The situation may be different if a mixture of a plurality of compounds has been taken up by the inert gas stream from the substance mixture. In this case, it may be desirable to release these compounds from the inert gas individually or at least in the form of several fractions of substance mixtures. If, for example, the new process is desired to be used in place of distillation for the separation of mixtures of materials, it may be desired to obtain several fractions of different volatilities as the result of the separation process. This is possible in the process of the invention by several routes.

Such a fractionation of mixtures of different materials can be achieved in a particularly simple manner by simply utilizing the principles or interrelationships described above. Since the quantity of material taken up is the greater the closer the process temperature used approaches the supercritical temperature, absorptive power of the supercritical gas increases as the operating temperature approaches this critical temperature. Reversely, the absorptive power becomes the lower the more the operating temperature exceeds the supercritical temperature. Furthermore, since the materials present in the inert gas are taken up more or less readily by the supercritical gas, decrease in absorptive power obviously has the result that portions of the materials taken up are not only released but that these portions are preferably those which are most difficultly taken up in the supercritical phase. This conception is confirmed by practice. It results in the simple operating rule according to which a mixture of materials is first taken up in a supercritical gas phase whereafter the temperature of this loaded gas phase is increased, especially in steps, thereby reducing its absorptive power. This has the result that portions of the mixture taken up are released proportionately to the increase in temperature in a manner such that initially the more difficultly absorbable, especially more difficultly volatile compounds are released preferentially whereupon the compounds of increasingly high volatility are obtained in steps as products of the separation process.

Exactly the same effect can be obtained by varying the pressure. However, this requires reduction in pressure. Advantage can be taken of this interrelationship or principle in the new process to realize fractionation of mixtures of substances by causing at least part of the mixture being separated to be taken up in the supercritical gas phase at pressures ranging sufficiently far above the critical pressure and thereafter reducing step by step the loadability of the supercritical gas phase by depressurization which again is preferably effected stepwise. Here again, the most difficultly absorbable and, in the normal case, less volatile compounds are released initially whereupon the compounds of increasing volatility are obtained in steps. Said depressurization may be continued until the gas is free from compounds to be separated. The same is true for the raise in temperature.

In a particular embodiment of the invention, these two principles or interrelationships can be combined to release the mixtures taken up, i.e. it is possible to effect said raise in temperature and said depressurization simultaneously to achieve specific and predetermined separating effects. Thus, this embodiment of the new process comprises separating mixtures of substances, particularly into fractions of different volatilities, by causing a mixture of substances to be taken up in the supercritical gas phase and subjecting the gas phase thus loaded to stepwise depressurization and/or stepwise increase in temperature. It is to be understood, of course, that this stepwise variation of operating conditions may be replaced by infinite variation of the conditions in the sense described above when taking care for withdrawal and separation of the fractions thus obtained.

The fractionation described above gives a certain separation into fractions, e.g. of different volatilities, but the process is not as efficient with respect to separating effect as is the known fractional distillation. It has been found that in effecting simply stepwise release of fractions from mixtures of substances taken up in the inert gas, very uniform release with respect to only one component cannot be achieved. While this separation by mere stepwise release may be adequate for many purposes, it may be desirable in other cases to make possible substantially more precise fractionaction of the mixture taken up. In accordance with the invention, this is also possible in a specific embodiment without any difficulty, and it appeared that even separation problems which cannot be solved by fractional distillation can be solved in accordance with the invention. In this embodiment of the invention, optimum separating effects in the sense of fractional separation of materials are obtained in a simple manner.

According to this embodiment, the process of separating mixtures of substances containing organic compounds and/or organic groups-containing mixed compounds comprises contacting an inert gas stream maintained under supercritical conditions of temperature and pressure with the mixture to be separated and loading it with at least part of the mixture of compounds to be separated, releasing in a separate step the compounds taken up in the supercritical gas and passing at least part of the released material into an exchange zone where it is contacted with the loaded gas stream under supercritical conditions for the inert gas used, and recovering the product of the separating process from said exchange zone and/or from said gas stream after it has left this exchange zone.

Here, the principle of the invention resides in the measure of contacting the loaded gas stream and the material released therefrom under supercritical conditions prior to recovering the product of the separation. The principle which is operative in this case is comparable with the fractionation principle in fractional distillation. In treating the mixture to be separated with the inert gas, this gas stream is loaded with a portion of the mixture of substances, the composition of this portion being normally different from that of the starting mixture. Since the compounds of higher volatility are more readily taken up, a higher amount of them as compared with that of the less volatile compounds will move into the inert gas stream. Thus, the mixture of material entrained by the loaded gas is enriched with components which are more readily taken up by the gas. If this mixture of substances is released and again contacted with an inert gas stream under supercritical conditions, the same phenomenon will occur, i.e. the loaded gas stream now withdrawn is again enriched with a still higher concentration of the component of higher volatility as compared with the starting mixture of this step. By constantly repeating these loading and release strokes, the component of higher volatility becomes more and more concentrated in the gas stream so that it can be recovered in increasingly pure state.

Based on experience from fractional distillation, it is preferred in accordance with the invention not to effect these alternating loading and release strokes in separate process steps but to combine any great member of these alternating steps in one process unit. In this process step which is referred to as exchange zone the loaded supercritical gas stream is exposed with a sufficiently large surface area to the released material recovered in the process subsequently to the exchange zone. Here, the exchange of load of the carrier gas stream can take place by the alternating processes described above, it being preferred in accordance with the invention to release from the carrier gas stream after passage thereof through the exchange zone at least a considerable part of the compounds taken up and to pass at least a considerable portion, but preferably all of this released material into the exchange zone where it is contacted with the loaded gas stream. In a particularly preferred embodiment of the process of the invention, the loaded gas stream and the released material are passed through the exchange zone in countercurrent flow relation. This relative movement of the materials which are being mutually exchanged results in an effect which corresponds to that of rectification in fractional distillation. Consequently, it may be preferred particularly in accordance with the invention to perform this exchange in rectification units known per se. Examples of suitable units of this kind include packed columns, bubble cap or sieve tray towers and cascade towers.

The processes on which the separation in accordance with the invention is based when effecting such rectification are best illustrated when taking the bubble tray column as an example. The loaded inert gas stream introduced at the base of the column changes its load between each two of the successive trays in that it becomes enriched with the more readily absorbable, i.e. more volatile compounds of the mixture of substances being separated. Consequently, in the direction to the top of the column, the liquid on the trays becomes more and more enriched with the lightest compound absorbable by the inert gas stream. Therefore, it is possible with a sufficient number of plates to withdraw from the top of the column an inert gas stream which contains substantially only this component which is most readily taken up by the gas. This component is released from the gas stream and at least a major part of it is returned to the top of the column. In this manner, rectification can be carried out in continuous operation.

Accordingly, in a particularly preferred embodiment of the invention, the supercritical gas stream loaded with the compounds to be separated is introduced at the base of a rectifying column maintained under supercritical conditions of the inert gas used. At the same time, the liquefied released material separated from the gas stream after the same has passed through the rectifying column is fed at the top.

The exchanged loaded gas stream is withdrawn at the top of the rectifying column, freed at least partially from compounds still contained in it, and the material thus obtained is returned at least partially into the rectifying column. A column reflux which, as the case may be, is withdrawn at the base of the column or also a portion of the column reflux withdrawn at a different point and not withdrawn as products of the separation process are preferably contacted again with the supercritical inert gas stream in the loading step. Of course, this is not indispensable, it being rather possible to carry out the process of the invention in the manner analogous to continuous distillation as it is carried out, for example, in continuously fractionating hydrocarbon fractions, e.g. petroleum products, on a commercial scale. In this case, the mixture of substances to be separated may be fed to the column at an intermediate point while the supercritical inert gas stream is passed through the column from below. Those compounds which are not capable of being taken up in the inert gas stream leave the column in downward direction while those compounds which are taken up by the gas are distributed in the inert gas to the extent of their absorbability and may be withdrawn therefrom.

Here again, separation of the inert gas stream leaving the exchange zone into the inert gas and entrained material is effected by raising the temperature, reducing the pressure or by a combination of these measures. This separation may be effected in one or two steps, it having been found that just a multistep separation may involve particular advantages from the process point of view. For example, two-step separation may be effected with preferably all of the material released in the first step and possibly part of the material released in the second step being returned into the rectifying column. The preferred place to introduce this reflux is the top of the column in both cases. Particular advantages are obtained in this case if, for example, the process is operated as follows:

First of all, most of the compounds taken up is released from the loaded and exchanged inert gas stream by raising the temperature. This portion is directly returned into the rectifying column. In order that this increase in temperature will not become excessive, substantially complete release is dispensed with intentionally in this phase. The inert gas stream now obtained is rather passed into a separate process step where further portions of entrained compounds still contained in the gas are released, this being desirably achieved by depressurization. Complete recovery in this step is achieved by reducing the pressure below the critical pressure. This may be preferred. The resultant constituents of the original load may either be recovered as product or at least part of them may be returned into the rectifying column to further increase the fractionating effect. For reasons of economy, the inert gas stream, after adequate compression, is returned, of course, to be loaded with further amounts of the mixture to be separated.

These explanations show that knowledge or experience and terms from fractional distillation are successfully applicable to the novel process of the invention although the individual phenomena on which the process is based are of a different nature. However, the possibility can be derived from analogy set forth above to solve the problems of fractional distillation via a novel route in continuous operation or with complete and batchwise separation of a predetermined amount of a mixture of substances.

Surprisingly, it has been found in case of the process of the invention that the exchange between the inert gas stream and that portion of the released material which is returned into the exchanger proceeds particularly easily. Consequently, outstanding rectifying results can be achieved with, for example, small packed columns which cannot be used in fractional distillation for corresponding separation problems. There are several suppositions as regards the reason of this surprising phenomenon. The fact that, in the process of the invention, the differences in density between the two phases being exchanged are substantially less than in case of conventional distillation will not be insignificant. The supercritical loaded inert gas has a considerably higher density than that of the vapor of the mixture to be separated operative in a corresponding manner in fractional distillation. This can be easily observed visually. It appears in fact that the liquid returned into the exchange zone drops to the bottom at a lower rate and in a more buoyant or suspended condition than does a reflux drop in conventional fractionating columns. Furthermore, it will not be unessential for this more rapid exchange that the exchange of liquid-in-gas phase in accordance with the invention does not require changes of energy which, as is known, play a decisive part for conventional evaporation and condensation in classical distillation.

It may be preferred in the process of the invention in analogy with the ideal classical fractionation tower to operate the exchange zone throughout with substantial variation of pressure and temperature. This means that additional fractionating effects by variation of these variables will not appear in the exchange zone. Thus, merely transloading of the inert gas stream will take place in this zone in the manner desired. Among the apparatus which are particularly suitable for this embodiment are packed columns.

On the other hand, an additional influence on the fractionating effect may also be exerted within the exchange zone by varying the pressure and the temperature. Particularly simple from the technological point of view is variation of temperature. In this case, the general rules are applicable, i.e. increase in temperature results in decreased absorptive capacity and consequently release of material while the same result is obtained by reduction in pressure.

It has been found surprisingly in this connection that it is possible to dispense with auxiliary means effecting an increase in surface area of the recirculated liquid when performing such a rectification, these means being usual in distillation. Thus, it is by no means necessary to use packed columns or exchange devices operating in an equivalent manner. It has been found to be sufficient for obtaining outstanding separating effects to set temperatures in the exchange zone which increase continuously or stepwise in a progressive manner. For example, the exchange zone may be heated in the manner desired with external means of by means of a heating cylinder inserted into the interior of the column. Increasing amounts of the compounds taken up are released as they move past the surfaces of the exchange zone which progressively increase in temperature, the released material flowing downwardly by gravity if liquids have been released. The possibilities, existing at these surfaces, for an exchange between the liquid reflux and the loaded supercritical inert gas stream rising in upward direction are sufficient for obtaining outstanding fractionating effects. It is also possible, of course, to keep the exchange zone under constant process conditions and to allow part of the material released outside the zone to flow downwardly at the walls of the exchange zone.

Similar to the case of fractional distillation, the separating result of a given column will be improved as the velocity of the rising loaded gas phase decreases so that it may be preferred to use a relatively slowly moving inert gas stream. Due to the high absorptive capacity of the supercritical inert gas, a sufficiently large amount of material is nevertheless entrained in upward direction through the column so that process results which are at least equivalent to those obtained in fractional distillation may be realized. In particular, it is possible by variation of the operating pressure to regulate the amount of material taken up in the inert gas stream, it being merely necessary to use sufficiently high pressures if the process is not satisfactory in this respect. In connection herewith, a measure is applicable which may be advantageous especially in batchwise rectification by the process of the invention: If the mixture of substances being separated becomes progressively poorer in compounds which are easily taken up, then that amount of the mixture being separated which is carried by the inert gas stream into the exchange zone per uniit time will decrease progressively under constant operating pressure. This phenomenon can be counteracted by progressively raising the pressure in steps or continuously. This increase in pressure corresponds to some extent to the increase in temperature of the bottoms in classical distillation. It is the purpose of both measures to introduce increased concentrations of those compounds into the separating zone which are increasingly difficult to pass into said zone.

As was mentioned above, this fractional separation may be carried out in batchwise and continuous operation. The difficulties which may be encountered in continuous operation even in case of the new separation principle are comparable with those offered by the well-known fractional distillation operated continously. Briefly, the following difficulties are involved:

Mixtures consisting of a plurality of substances, e.g. natural or synthetic mineral oils or fractions recovered therefrom, tars, etc., can be separated into different fractions in a single operation by providing points of withdrawal at the column at different levels.. The individual fractions can be obtained from the column simultaneously with a single distillation since the lower boiling compounds of the mixture being separated rise upwardly to higher plates while the lower boiling constituents accumulate on the lower plates. Thus, the great number of constituents are spread apart by the column in an order which approximately corresponds to their boiling points. However, sharp separation is not possible in this manner, it being necessary for the low boiling constituents in case of the withdrawal of several side streams to be present on all plates of the column since, in continuous operation, they must migrate in upward direction through all parts of the tower. Thus, the fractions obtained from the lower plates must contain in any case a more or less large portion of the lower boiling compounds of the mixture. For an actually efficient separation, all or at least part of these portions must be removed in order that the side fractions withdrawn from the column have the initial boiling point desired.

For this purpose, the system of well-known strippers was developed in conventional distillation technology, a sufficient number of strippers being connected, for example, to a continuously operating rectifying column. When operating in this manner, the side stream withdrawn from the column is subjected to subsequent stripping. The low boiling constituents thereby separated from the product desired are again introduced into the rectifying column at a point located above that where the side stream is withdrawn and are thus retained in the separation process. The product desired is withdrawn from the stripper as the bottom fraction.

These difficulties which are typical of the continuous fractional distillation are also inherent in the continuous distillation process of the invention. Here again, the mixture of substances being separated is spread apart in the interchange zone. If it is desired to withdraw side streams of product at one or more levels of this interchange zone, these side streams necessarily contain more or less large portions of the products being present in the interchange zone above the point of withdrawal. Therefore, the products obtained continuously in the process of the invention must also be improved with respect to their composition. In accordance with a further development of the process, this can be achieved by utilizing a simple principle which can be satisfied by several specific modes of operation.

Accordingly, an object of this embodiment of the invention is a process for the separation of mixtures of substances containing organic compounds and/or organic groups-containing mixed compounds by contacting an inert gas stream maintained under supercritical conditions of temperature and pressure with the mixture to be separated and loading it with at least part of the compounds to be separated, releasing separately herefrom the compounds taken up in the supercritical gas, contacting in an interchange zone at least part of the released material with the loaded gas stream under supercritical conditions for the inert gas used, and recovering the product of the separation process from the interchange zone and/or the gas stream after it has left the interchange zone, the process comprising withdrawing mixture of substances from the interchange zone at the particular point of withdrawal (1st separation step), subjecting this mixture to an additional separation (2nd separation step) thereby recovering the separated product desired, and returning the remainder of the compounds from the 2nd separation step preferably into the first separation step. Thus, in case of this embodiment of the new process, a second separation step effecting the separation desired of the product stream withdrawn from the interchange zone is added to the new fractional separation referred to herein as the first separation step. For continuous operation of this embodiment of the invention it is preferred to introduce the loaded inert gas stream continuously into the interchange zone of the first separation step while, at least at one point which is spatially separated from the point where the inert gas stream is introduced, mixture of substances present at said first-mentioned point is withdrawn from said interchange zone. This mixture is subsequently passed to the 2nd separation step where it is separated into at least one more volatile part which is more readily taken up by the supercritical inert gas and at least one less volatile part which is more difficultly transferred into the supercritical inert gas. All or part of the less volatile portion thus obtained is withdrawn as the separated product desired of the new process. The remaining residue of the second separation step is preferably returned into the first separation step. In this manner, the recovery of the separated product desired in the purity required is ensured and, moreover, no portions of the mixture being separated are lost from the separation process while continuous operation is also ensured.

The second separation step may be operated in conventional manner. Thus, for example, if such a mixture which has been pre-separated in the first step is available, this mixture can be separated into desirable and undesirable components by methods known from fractional distillation. For example, this separation may be effected with conventional strippers. Of course, a conventional distillation operation or other well-known separation processes may be used in connection with the second separation step of the process of the invention.

However, the features of the new process permit a particularly simple, efficient and economic aftertreatment in the second separation step if the principles described above are again utilized. In a particularly preferred embodiment of the new process, both the first separation step and the second separation step are operated in accordance with the fundamentally novel separation principle. This embodiment exhibits great differences from the multi-stage separation process based on fractional distillation and subsequent stripping.

It is a typical feature of conventional fractionating columns that the side streams are withdrawn from the liquid phase trickling downwardly inside the column. For example, they are withdrawn from the liquid contained on the individual plates of such a rectifying column. It is also possible in case of the process of the invention to withdraw portions of the liquid phase in a corresponding manner within the interchange zone at one or more points and to process them in the above-mentioned second stage into the product desired. However, in a particularly preferred embodiment of the new process, those portions of the mixture of substances which are to be transferred into the second separation stage are not withdrawn from the liquid phase but from the supercritical gas phase of the interchange zone. This is preferably achieved in a simple manner by splitting off portions of the loaded inert gas stream present at the particular point of withdrawal inside the interchange zone and removing them from the interchange zone. Thus, there are simply withdrawn portions of the loaded inert gas stream which, however, differ from the loaded starting gas stream with respect to the compounds taken up. Those portions of the inert gas stream which are withdrawn from the interchange zone have already undergone a phase with the liquid phase of the interchange zone and changed accordingly in their composition. Since the inert gas stream is enriched more and more in more volatile or more readily absorbable compounds of the mixture being separated while said stream passes through the interchange zone, the inert gas portions withdrawn will accordingly contain progressively increasing amounts of the more volatile or more readily absorbable compounds, these amounts increasing to the extent to which the exchange between the supercritical gas phase and the returning liquid could take place.

Thus, the particularly preferred embodiment of the invention does not give a liquid as the preliminary product of the separation in the first separation stage but a supercritical gas stream which, while containing a mixture of compounds which is already improved with respect to its composition, nevertheless requires further separation of these compounds.

This is achieved by taking advantage of the rule or principle described above, i.e. that the absorbability of a specific compound increases with increasing pressures of the supercritical gas above the critical pressure and decreases with increasing temperatures above the critical temperature.

This effect is utilized in the particularly preferred embodiment of the new process described above, viz. within the second separation stage. In this second stage, the less volatile or more difficultly absorbable portion of the compounds is released from the inert gas side stream by increasing the temperature and/or reducing the pressure, the extent of the changes of these variables being only such, however, that only partial release of the compounds taken up in the inert gas is ensured. The effect of this partial release corresponds to that of a conventional stripper. The process of the invention has the additional advantage that the undesirable, more volatile or readily absorbable compounds are retained by the inert gas stream also after the second separation stage so that this inert gas stream needs merely be returned into the exchange zone to avoid undesirable losses. It is previously necessary, of course, to equalize the temperature and/or the pressure of this inert gas stream from the second separation stage with the corresponding conditions of the first separation stage. Since this residual gas stream is preferably returned into the interchange zone of the first separation stage, it is merely necessary to reset these values of the exchange zone, which can be achieved, for example in an energy-saving manner by heat exchange with the side gas stream withdrawn from the exchange zone.

When returning the more volatile compounds obtained in the second separation stage in addition to the product desired into the exchange column within the inert gas stream it is particularly preferred in accordance with the invention to feed these compounds to the exchange column at a point which has a greater distance from the point where the initial loaded inert gas stream is introduced than the point where the mixture treated in the second separation stage is withdrawn. The following rule results from this teaching for the particularly preferred embodiment of the separation process of the invention: In the first separation stage, use is made of a vertical exchange zone, e.g. a separation column, from which portions of the loaded inert gas stream are withdrawn as side stream. Part of the compounds taken up is released from these partial gas streams, particularly by depressurization and/or increase in temperature, this part being thus obtained as the separated product desired, following which the inert gas partial stream thus partially freed, if necessary after sufficient compression and/or decrease in temperature, is returned into the interchange zone above the point where the partial gas stream is withdrawn.

In addition to the principles of general validity described above, the process of the invention exhibits a number of features which may be essential in individual cases. For example, it has been found that the amount of a substance which is relatively difficultly taken up by the supercritical gas can be increased in this gas phase by causing more readily absorbable compounds to pass into the supercritical gas phase together with the compound which is difficultly taken up. Thus, compounds which are more readily taken up, especially those of higher volatility, are simultaneously used to increase the absorbability in the supercritical gas phase.

It is not intended at this place to discuss the manner how this phenomenon is to be valued. As a matter of fact, it is possible, for example, that considerable amounts of complicated organic natural substances having a great number of carbon atoms in the molecule can be caused to pass over into the supercritical gas phase with the aid of more volatile compounds. An impressive example is the removal of chlorophyll from comminuted plant parts by means of a supercritical gas to which organic compounds of higher volatility have been added.

It is desirable to use for this purpose an auxiliary agent of higher volatility which is readily separated from the less volatile compound under normal conditions, e.g. by conventional distillation. Thus, the invention provides the possibility to separate compounds of low volatility from accompanying substances by a process which is comparable with distillation, this process being widely applicable to an extent which the conventional separation processes do not permit. The advantages which may thus be involved in the new process in specific fields, e.g. in the field of natural substances, become clearly obvious when considering that, with a suitably selected supercritical gas, the process can, for example, be operated at room temperature with maximum efficiency. Thus, the invention offers the possibility to isolate substantially non-volatile substances at room temperature through the intermediary of taking these substances up in a gas phase. Further explanation regarding the novel technical possibilities which the invention opens in many fields of natural sciences is unnecessary. Of course, the new process is by no means restricted to the field of natural substances mentioned above but of general applicability.

Another remarkable phenomenon is as follows: The first step of all methods described above comprises loading of the inert gas with at least part of the compounds which are capable of being taken up by the inert gas. This loading step may be performed by different methods. For example, the mixture of substances to be separated may be fed intermittently or preferably continuously to a loading zone where it is contacted with a separating gas stream which is preferably passed through continuously. This gas stream will then take up the compounds being separated and it may be preferred in this case to keep always available in the separating zone an excess of separating gas so that the portions of the mixture of substances to be separated and introduced per unit time are actually taken up by the separating gas as far as this is possible at all.

Another method of loading the gas phase which may frequently be preferred in practice is as follows: A given amount of the mixture to be separated is previously introduced whereupon a stream of the separating gas is passed through. In this case, the separating gas is not intended to take up all of the mixture at a time but should become loaded to an extent only which corresponds to its loadability under the process conditions. These portions are then passed to the separation process. It is an essential condition in this case that the loaded gas stream separates as a separate phase from the liquid or solid mixture of substances, for only if this separation of the loaded supercritical gas stream from the bulk of the mixture to be separated is successfully achieved, the purpose of this modification can be attained, i.e. to gradually take up the mixture to be separated into the supercritical gas stream and then gradually introduce it in this form into the separation process. It appeared, however, that a disturbance may occur in the loading step in case of specific mixtures of substances, especially in case of liquid mixtures. As a rule, this disturbance evidences itself by the following phenomenon:

If, at the supercritical operating temperature, the separating gas is forced into the pressure vessel in which the gas is loaded with components of the mixture to be separated in order to reach the critical pressure and enter the operating range of the process of the invention, it may happen under circumstances already at pressures below the critical pressure that the volume of the liquid mixture charged starts to increase and continues to do so with increasing pressures with substantially no limit. Some increase in volume will always occur during the treatment with the separating gas. However, this is normally only a limited increase in volume. The further compression and passing-through of the separating gas are then accomplished without any difficulties. For example, the gaseous phase may be bubbled through the liquid thereby becoming loaded with portions of the compounds of the liquid phase to be separated. However, in the anomalous case mentioned above, this growth of the liquid phase is substantially unlimited. Further introduction of separating gas under pressure does not only result in separation of a gaseous phase but also in a continued growth of the liquid phase and eventually the liquid passes over into a gaseous state. This state having been reached, separation into the loaded supercritical gas phase and the remainder of the mixture of substances is no longer possible. In both the normal case and the anomalous case of interest in connection with the invention, this growth of the volume of the liquid charged is doubtlessly due to solvation effects between the compounds of the mixture to be separated and the separating gas, these effects having the undesirable result in said anomalous case that separation into liquid and gaseous phases cannot be accomplished. When using, for example, lower hydrocarbon compounds such as ethylene or ethane which are particularly important in practice, this phenomenon will frequently appear if lower boiling pure hydrocarbon compounds are treated. Here, a definite principle or interrelationship seems to be applicable to the occurrence of these disturbances or anomalous cases. As a rule, this undesirable phenomenon will occur with compounds which are taken up particularly readily by the supercritical gas. Since, in general, volatility of the compounds to be separated is directly proportional to their capability of being taken up in the supercritical gas, the rule applies that this disturbing effect will preferably occur with compounds which have a considerably inherent vapor pressure under the process conditions. Thus, when operating with, for example, ethylene or ethane, the interference will preferably occur with pure hydrocarbon compounds of higher volatility. In special cases, corresponding interferences may also be encountered with higher boiling compounds. An example illustrating this case will be given hereafter.

It is very striking that the tendency of the interference to occur becomes substantially lower if the compounds to be taken by the separating gas contain groups which are more difficultly amenable to solvation by the separating gas. When operating with ethylene or ethane as the separating gas, typical examples hereof include hydrocarbon compounds which bear groups containing hetero atoms such as amino groups, hydroxyl groups, nitro groups, carboxyl groups, etc. This is illustrated in a particularly impressive manner by the following example: When operating at room temperature (about 25°C.) with ethylene as the separating gas, cyclohexylamino which boils at 134°C. can be taken up without any difficulty in a supercritical ethylene stream which separates from the remaining liquid phase. In contrast, when using a pure hydrocarbon boiling at about the same temperature, the interference effect described above may occur unless special precautionary measures are taken, i.e. when adding ethylene under pressure to this mixture of substances, the liquid volume will grow to an increasing extent and separation of a loaded supercritical gas phase is impossible.

It is easily possible in accordance with the invention to eliminate the interference described above in the loading step irrespective of where this interference effect occurs. It has been found that the undesirable growth of the liquid volume can be prevented in a simple manner by admixing compounds which do not show this interference in the supercritical gas phase with the mixture of substances apt to such interference, said mixing being effected in the loading step. Preferred additives are those which can be mixed homogeneously with those compounds of the mixture being separated which are subject to the interference. It appeared that the interference mentioned above can always be eliminated when using this expedient.

There is a great number of examples hereof in practice. A typical example is the separation of petroleum or comparable synthetic hydrocarbon mixtures. In this case, the raw material obtained with its natural distribution of volatility is treated with the supercritical separating gas. As is known, crude oil contains considerable amounts of low boiling hydrocarbon compounds, especially compounds boiling in the gasoline and naphtha range. Despite this fact, loading of the inert gas and subsequent separation of the loaded gas from residual crude oil is accomplished without any difficulty by effecting the loading in the presence of the higher boiling components of the crude oil which are more difficultly taken up in the supercritical gas and do not show the interference effect. The presence of these compounds prevents the interference effect from occurring when loading the separating gas with the lower boiling compounds. The situation is similar in other simpler cases, e.g. in the treatment of a mixture of dodecene and paraffin oil (paraffinum liquidum). Dodecene alone may show the undesirable interference effect when treated with ethylene. In the presence of paraffin oil which has a substantially higher boiling point and does not lead to this interference, reception in the ethylene gas is accomplished without any difficulty.

It is preferred in accordance with the invention to use auxiliary substances in the loading step which are more difficultly taken up than the mixture of substances being separated. When operating in this manner, the loading step is carried out with no interference and, in addition, this auxiliary substance is readily separated from the mixture to be separated. In this aspect of the invention, it is preferred that the auxiliary substance is not allowed to pass through the separation stage but is always retained in the loading step. This is achieved by simply discontinuing the separation process as soon as the compounds which are more readily taken up have passed through the separation stage.

As mentioned above, the two indispensable requirements to be met by the substances used as auxiliary agents in accordance with the invention are firstly that they do not show the interference effect with the supercritical gas and secondly that they can be mixed homogeneously with substances which are subject to the interference. Thus, it is not only possible to use less volatile homologues or related compounds of the compounds being separated as auxiliary substances which do not show this interference effect, recourse may also be had to the previously mentioned classes of substances which, due to their constitution, are less apt to undesirable solvation effects. Non-restrictive examples for operation with hydrocarbon gases include compounds such as amines, nitro compounds, alcohols, carboxylic acids and derivatives thereof and the like.

The amount of auxiliary substance necessary in each case to suppress the interference can be easily established in a preliminary experiment. The minimum amount is determined by the degree to which this auxiliary substance resists the interference effect. The amount of the auxiliary substance used may be decreased as its resistance to the interference increases. There is substantially no upper limit on the amount added of this auxiliary substance. It is determined by economic considerations. The rate of addition is easily determined by a simple preliminary test in which the mixture of substances subject to the interference is mixed with increasing amounts of the auxiliary substance and then treated with the separating gas. As a rule, satisfactory results are obtained when the mixtures to be separated and the auxiliary substances are mixed in a ratio of 1:1. However, in general, these high amounts of auxiliary substance are not even necessary. Normally, very much lower amounts of the auxiliary substance are sufficient to eliminate the interference effect.

Another important special case of the process of the invention which may be of technical importance in individual cases is illustrated by the following specific examples:

It is known that aluminum alcoholates can be prepared by oxidation of aluminum trialkyls. It may be desirable in this case to prepare higher aluminum trialkyls in what is known as the growth reaction by addition of ethylene to lower aluminum trialkyl compounds. This reaction first yields higher aluminum trialkyls which are then converted into the corresponding aluminum alcoholates by oxidation in a manner known per se. It is known that more or less large amounts of free hydrocarbons, especially free olefins, are concomitantly produced in this process by displacement reactions which per se are indesirable. Distillation is an expedient which permits only partial separation of these olefins from the higher aluminum trialkyls or aluminum alcoholates, considerable amounts being retained by the aluminum alcoholate so tenaciously that substantial amounts of higher hydrocarbons which are no longer separable by distillation are admixed with the free alcohols obtained after hydrolysis of the aluminum alcoholates. Thus, contaminated products are obtained. It has been found that the process of the invention is an efficient remedy to this drawback.

As was explained above on the example of polyfunctional alcohols, compounds are not taken up by specific supercritical gases in special cases even though this exceptional behaviour would not be expected from the volatility of these compounds and their other chemical constitution. It was explained that, for example, polyhydric alcohols such as glycols or glycerol are not taken up by simple hydrocarbon gases such as ethylene or ethane. This must be due to additional intermolecular forces between the individual molecules of the polyfunctional alcohol which prevent sufficient solvation and detachment of the individual molecule from its association with the adjacent molecules.

An analogous phenomenon is shown by aluminum alcoholates when treated with supercritical hydrocarbon gases such as ethylene or ethane. Here again, substantially no aluminum alcoholate is taken up by the supercritical gas phase even though the constitution of these compounds would suggest their reception by the gas phase. Here again, additional intermolecular forces between the individual molecules of the aluminum alcoholate are supposed to constitute an additional barrier which leads to the unexpected result.

However, the absorptive capacity of a supercritical hydrocarbon gas for other hydrocarbon compounds mixed with the aluminum alcoholates is unaffected by this phenomenon. Accordingly, if a gas such as ethylene or carbon dioxide is passed under the conditions of this invention through the aluminum alcoholate reaction mixture prior to hydrolysis, the organic impurities which are chiefly olefins are taken up in the supercritical gas phase substantially quantitatively while the aluminum alcoholate is obtained as the residue. In this manner, separation of undesirable by-products from aluminum alcoholate is easily accomplished.

The aluminum alcoholate itself may be subsequently subjected to the process of the invention thereby effecting, if desired, separation into alcoholates of different alcohol chain lengths, it being only necessary for this purpose to select a supercritical gas phase which is capable of breaking the additional intermolecular forces between the individual aluminum alcoholate molecules. Here again, ammonia under supercritical conditions is suitable. Similar to polyfunctional alcohols, aluminum alcoholates are readily taken up by the supercritical ammonia gas phase and may accordingly be subjected to the separation process of the invention in this form.

The embodiment of the invention described above with reference to a specific example is of importance for any mixture of substances which, when treated with a specific supercritical gas, is taken up only partially by this gas phase while the remainder may subsequently be taken up in a different supercritical gas phase.

Generally, the separation of mixtures of substances consisting entirely or preponderantly of hydrocarbon compounds is an application of greatest importance for the process of the invention. These mixtures of hydrocarbon compounds of greatest diversity are to be handled in chemical industry in so many different variations that it is unnecessary to quote specific examples. There may merely be mentioned a field which is industrially particularly important, i.e. the separation of petroleum hydrocarbons or of corresponding synthetic hydrocarbon mixtures. In this case, the crude oil or petroleum fractions may be the starting material subjected to the process. It is also known that the necessity is frequently encountered to separate product mixtures derived from the conversion of petroleum hydrocarbons or from the production of synthetic hydrocarbon mixtures. In all these cases, the performance of the process of the invention is unique and novel. It was already mentioned above that, especially in connection with the treatment of crude oil, even those fractions may pass over with the supercritical gas phase which are no longer separable from the starting material by conventional distillation techniques. It is obvious that novel routes are opened by the invention just in this field of petroleum processing.

The advantages of the process of this invention are of revolutionary importance and so numerous that they cannot be overlooked at all at this time. Of primary importance is the fact that separation operations can be carried out, the process results of which correspond more to those of distallation rather than extraction, but which nevertheless can be carried out throughout at any predetermined temperature, e.g. at room temperature. It is possible in this manner firstly to eliminate all those disadvantages which are normally encountered by heavy thermal stress of the mixtures to be separated and, secondly, considerable economy of energy can be achieved with the process of the invention. The new process may especially find important application in all fields where distillations had to be effected so far at high temperatures or even under vacuum. It was further described that the new process offers by far more possibilities of effecting separations than are offered by conventional distillation under atmospheric pressure or under vacuum. It is possible by the process of the invention to separate mixtures of substances which cannot be separated by distillation. Absolutely novel possibilities are also offered, for example, in the field of natural substances where the preparation of complicated great molecules in pure form becomes possible under careful thermal conditions. The extent to which preparative chemistry and chemical engineering will be influenced and enriched by the new process is still out of sight.

The principles on which the performance of the new separation process is based are further illustrated with reference to the accompanying FIGS. 1 to 5.

FIG. 1 shows diagrammatically a simple device for carrying out the process of the invention in solving simple separation problems and especially for use in those cases where a simple preliminary experiment is carried out to determine whether or not the mixture to be separated is suitable for use in the process of the invention. Inert gas maintained under supercritical conditions of pressure and temperature is passed through line 11 connected with manometer 12 and valve 13 and into the pressure vessel 14. This vessel is filled with a sample of the mixture of substances to be separated, care being taken in normal cases that a sufficiently large space is left free between the surface of the mixture to be separated and the upper wall of the vessel to have sufficient space for the increase in volume of said mixture which normally occurs when treated with the supercritical gas. The pressure vessel 14 may be provided in its interior with an agitator 15 which, for example, is rotated by the drive mechanism 16. The pressure in the vessel is controlled by means of a manometer 17. The vessel 14 is maintained at the operating temperature desired by means of a temperature control device (not shown). Examples of suitable media in the simple case represented in FIG. 1 include baths of conventional heating or cooling liquids.

The stream of supercritical gas introduced through line 11 enters the mixture to be separated at the base of the pressure vessel 14, passes through said mixture in upward direction due to its lower density and leaves the pressure vessel through line 18. In passing through the compounds being separated under the supercritical conditions maintained in accordance with the invention, the gas stream becomes loaded with part of the contents of the vessel provided that compounds are present which are amenable to the separation process of the invention under the process conditions maintained. Whether or not this is the case can be easily established by actuating the valve 19 which effects an adequate depressurization so that least part of the components taken up by the supercritical gas stream is released and accumulated in the receiving burette 20. From this burette, the released material can be withdrawn through 21. After complete or extensive unloading, the gas stream passes through 22 into the flow meter 23 and leaves the latter through 24. This gas stream is compressed in a compressor unit (not shown) and returned into the cycle through 11. It is easily possible by adjustment of pressure and temperature in the vessel 14 and by measuring the amount of compounds taken up per unit quantity of the inert gas stream, which amount is released in 20 and measured by the measuring device 23, to determine the extent to which the compounds to be separated are taken up by the supercritical gas stream under the particular conditions of pressure and temperature. The apparatus described above may also be used to solve simple separation problems. For example, if a mixture of compounds which can be taken up and compounds which cannot be taken up by the gas is contained in the vessel 14, the compounds which can be taken up leave the vessel 14 through 18 while the compounds which cannot be taken up remain in the vessel. The situation is similar if the compounds contained in vessel 14 are very different with respect to the degree they are capable of being taken up in the gas. Then such a combination of pressure and temperature of the supercritical gas stream can readily be used initially that substantially only the readily absorbable compounds passes over and, after the latter has been removed, the pressure in vessel 14 is increased to a level at which difficulty absorbable compound is also driven over.

Figure 2:
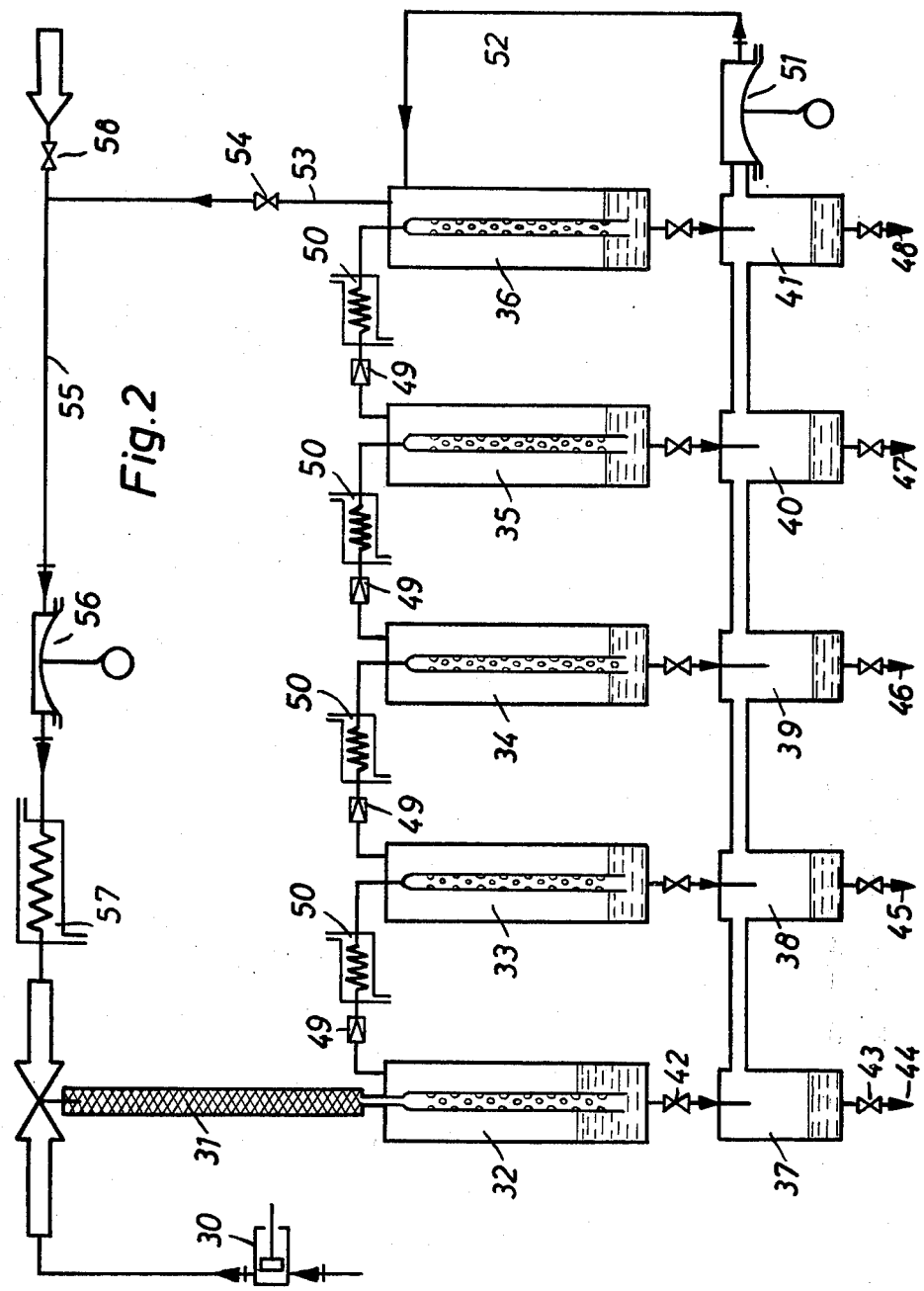
Figure 3:
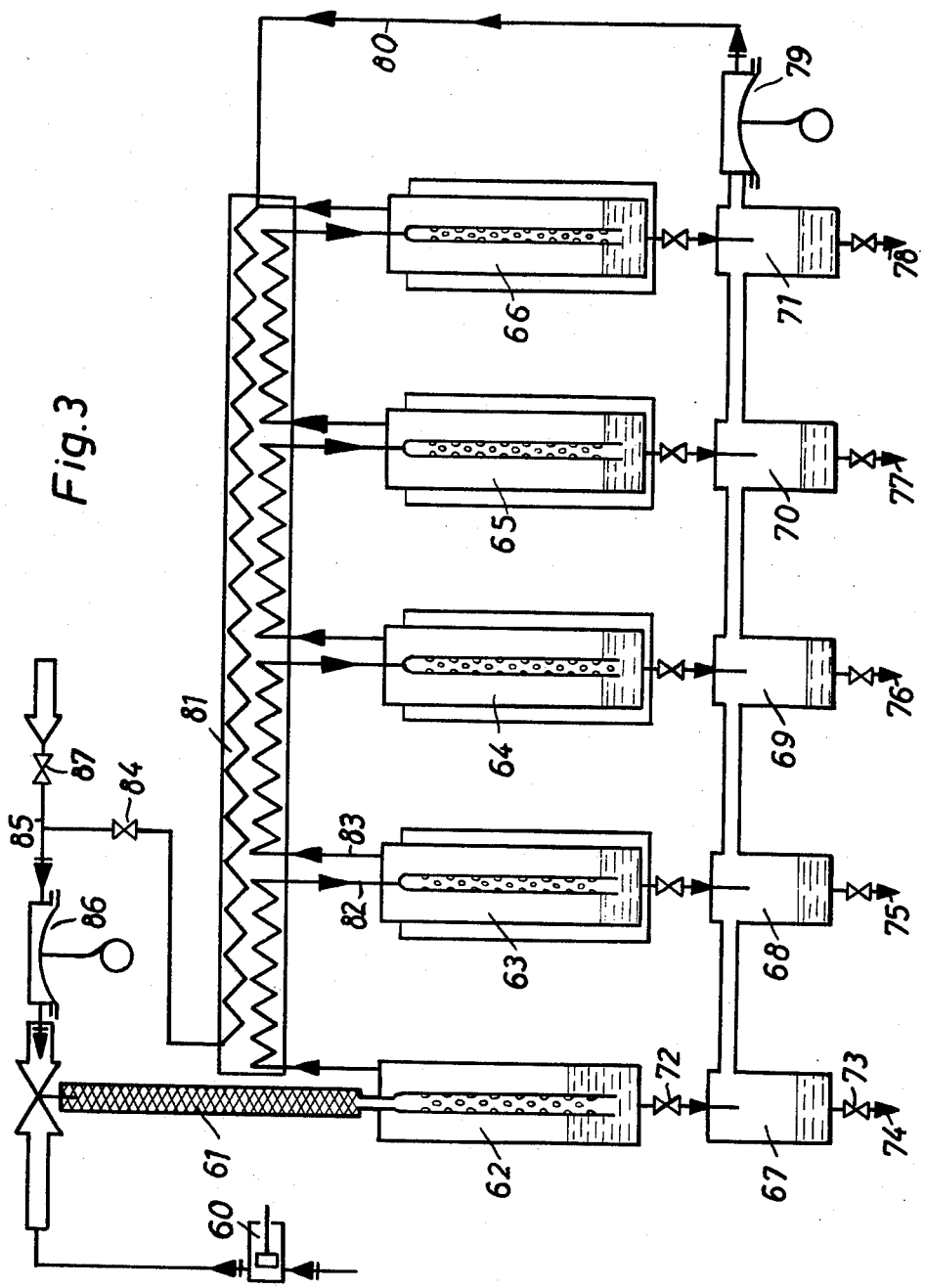

FIGS. 2 and 3 show diagrammatically two process cycles permitting stepwise release of compounds from a loaded supercritical gas stream in accordance with the invention, which stream contains a plurality of compounds of different absorbability.

FIG. 2 shows a mixing device 31 in which the mixture to be separated and introduced through 30 and the stream of supercritical separating gas are contacted. In this mixing device 31, the mixture to be separated may be taken up completely or partially by the supercritical inert gas stream.

32 to 36 are pressure separators, 51 and 56 are gas compressors, 37 to 41 are receivers associated with the pressure separators located above the receivers from which different fractions of the mixture being separated 44 to 48 may be withdrawn through valves 43. Release valves 49 are provided between the pressure release vessels 32 to 36. Each release valve 49 is followed by a heat exchange element 50 which in turn (by means not shown) may be arranged in heat exchange relationship with heat exchange element 57. For example, the temperature equalization coils 50 and 57 may be immersed in a common liquid bath held at the operating temperature desired. Furthermore, the pressure separators 32 to 36 may also be maintained at the operating temperature desired by temperature control means (not shown). This measure ensures that the operating temperature desired is maintained throughout the apparatus. Heat exchange between members 50 and 57 is important from the energy point of view. In this manner, the heat equalization coil 57 transmits heat of compression evolved by compression of the inert gas in 56 to the heat equalization coils 50 which are cooled by partial depressurization of the inert gas.

Initially, the entire unit is filled with the supercritical gas desired through inlet valve 58, line 55 and compressor 56. The partial depressurizations may be ensured in pressure separators 33 to 36 by means of the release valves 49. The following data are given by way of example:

The inert gas used may be ethylene having a temperature of 20°C. and being introduced until the pressure is 120 atmospheres in mixer 31 and pressure separator 32; 110 atm. in pressure separator 33; 95 at. in pressure separator 34; 70 atm. in pressure separator 35, and 40 atm. in pressure separator 36. Now valve 54 is opened while valve 58 is closed and the ethylene is recirculated in the system via the compressor 56. The relief valves 49 are set such that the pressure desired is always kept constant in the pressure separators even while ethylene is circulated. The mixture to be separated is now introduced continuously or intermittently by pump 30 into mixer 31 and consequently into this ethylene cycle. During this starting phase, the pressure initially rises in the system. Excess ethylene is withdrawn through valve 58. Fresh ethylene which may be necessary in the process may be fed through this valve from time to time. After about one fifth of the volume of all pressure separators is occupied by the liquid phase, substance in an amount equal to that supplied to the mixer 31 is continuously withdrawn from the pressure separators through the valves 42, i.e. the pressure will now remain constant in the system.

The mixer 31 is directly connected with the pressure separator 32. The latter and the pressure separators 33 to 36 downstream thereof consist of a pressure vessel into which a perforated tube is inserted from above. An opening in the top wall serves the withdrawal of the partially depressurized supercritical ethylene phase and an opening in the bottom is provided for the removal of the compound separated in the particular pressure separator. In the pressure separator 32 the compounds which were not taken up by the supercritical gas stream separate from the loaded supercritical gas stream. The latter passes in succession through relief valves 49 into the successive partial depressurization steps, in each of which that portion of the original load of the ethylene stream is released which was most difficultly taken up by the latter. This process of stepwise release is repeated until the pressure separator 36 is reached in which only a pressure of about 40 atm which is lower than the critical pressure is prevailing. Under this pressure the remainder of compounds taken up is released. The ethylene gas stream is returned to the mixing zone 31 through 53, 54, and 55.

The fraction of the starting mixture accumulating in pressure separators 32 to 36 are withdrawn intermittently or continuously into the associated receivers 37 to 41 which are under atmospheric pressure. In doing so, the ethylene still dissolved in the compounds withdrawn escapes and is returned into the circulating inert gas via compressor 51 and line 52.

The apparatus described above with reference to FIG. 2 and the separation process described in connection with the use of ethylene, similar to the apparatus and process described hereafter with reference to FIG. 3, are particularly suitable for processing mixtures of substances to be separated into a number of fractions. In particular, mixtures of hydrocarbon compounds can be separated into fractions in a particularly simple manner. A particularly important example in this connection is the processing of petroleum, petroleum fractions or petroleum products. It has been found that an astonishingly sharp separation of, for example, crude oil is obtained even with this relatively simply operated setup of the new process. For example, crude oil or crude oil fractions or petroleum products may be fed by means of pump 30 and then separated into different fractions by selecting a proper balance between the pressure and temperature in dependence upon the inert gas used. It is obvious that this is a particularly simple and economic process because nothing else is necessary than to load the inert gas stream once with the compounds to be separated and then merely direct the unloading or release in steps in such a way that the fractionating effect desired is obtained.

The process cycle diagrammatically shown in the accompanying FIG. 3 corresponds to that of FIG. 2 as regards the essential setup. The fractionating method represented in this drawing differs from that of FIG. 2 merely in that stepwise release of the compounds taken up in the inert gas is effected by stepwise increase in temperature and not by stepwise depressurization.

Here again, there is provided the loading device 61 to which the mixture to be separated and the supercritical inert gas are fed by means of pump 60 and compressor 86. Stepwise release of the fractions desired is effected in depressurization vessels 62 to 66, a temperature control device surrounding pressure separators 63 to 66 being indicated in this case. The pressure separators 62 to 66 are directly interconnected through a common heat exchanger 81. The heat exchanger consists, for example, of helical copper tubes which are embedded in tin to improve mutual heat transfer.

Here again, a process cycle is explained in connection with the use of ethylene as an example. The pressure separator 62 is kept, for example, at room temperature, i.e. about 20°C., the other temperatures being 50°C. for pressure separator 63 which is provided in this case with a heating bath; 80°C. for pressure separator 64 using also a heating bath; 110°C. for pressure separator 65, and about 140°C. for pressure separator 66. For starting up the unit, the entire apparatus is again filled with ethylene through inlet valve 87 and line 85 until a pressure of, for example, 120 atm is reached. Thus, in this case all of the pressure separators are under the same pressure but at different temperatures. Valve 84 is now opened to recirculate ethylene through the apparatus by means of 86 which is not a compressor as in case of FIG. 2 but merely a gas recycling pump operating under pressure. This gas recycling pump 86 draws the hot supercritical ethylene from pressure separator 66 through hat exchanger 81 and delivers it to mixer 61 after heat exchange, its temperature being now about 20°C. The compressed ethylene passes through the mixer and into the pressure separator 62 and thence into the common heat exchanger 81 where it is heated to about 50°C. and into pressure separator 63. From the latter, it passes again through the common heat exchanger and into pressure separator 64 and so on until it has reached the pressure separator 66. The necessary increase in temperature between the individual pressure separators is accomplished in each case in heat exchanger 81 through which the hot ethylene withdrawn from 66 is passed countercurrently to the loaded ethylene stream thereby realizing the heat exchange desired. Any additional minor corrections of the temperature which may become necessary can be made by means of additional heaters provided between the individual pressure separators. The mixture to be separated, e.g. crude oil or a petroleum fraction, is supplied to mixer 61 by means of pump 60. The further course of the process is then the same as that represented in FIG. 2. Those components which have the highest boiling points, i.e. which are most difficultly taken up by the gas, are separated in the pressure separators 62 to 66. Hereagain, the compounds released in the pressure separators are withdrawn through valves 72 into the associated receivers 67 to 71. Any ethylene which may escape in these receivers, is withdrawn by compressor means 79 and returned into the ethylene cycle. Fractions 74 to 78 obtained in this separation process may be withdrawn from the receivers through valves 73.

Figure 4:
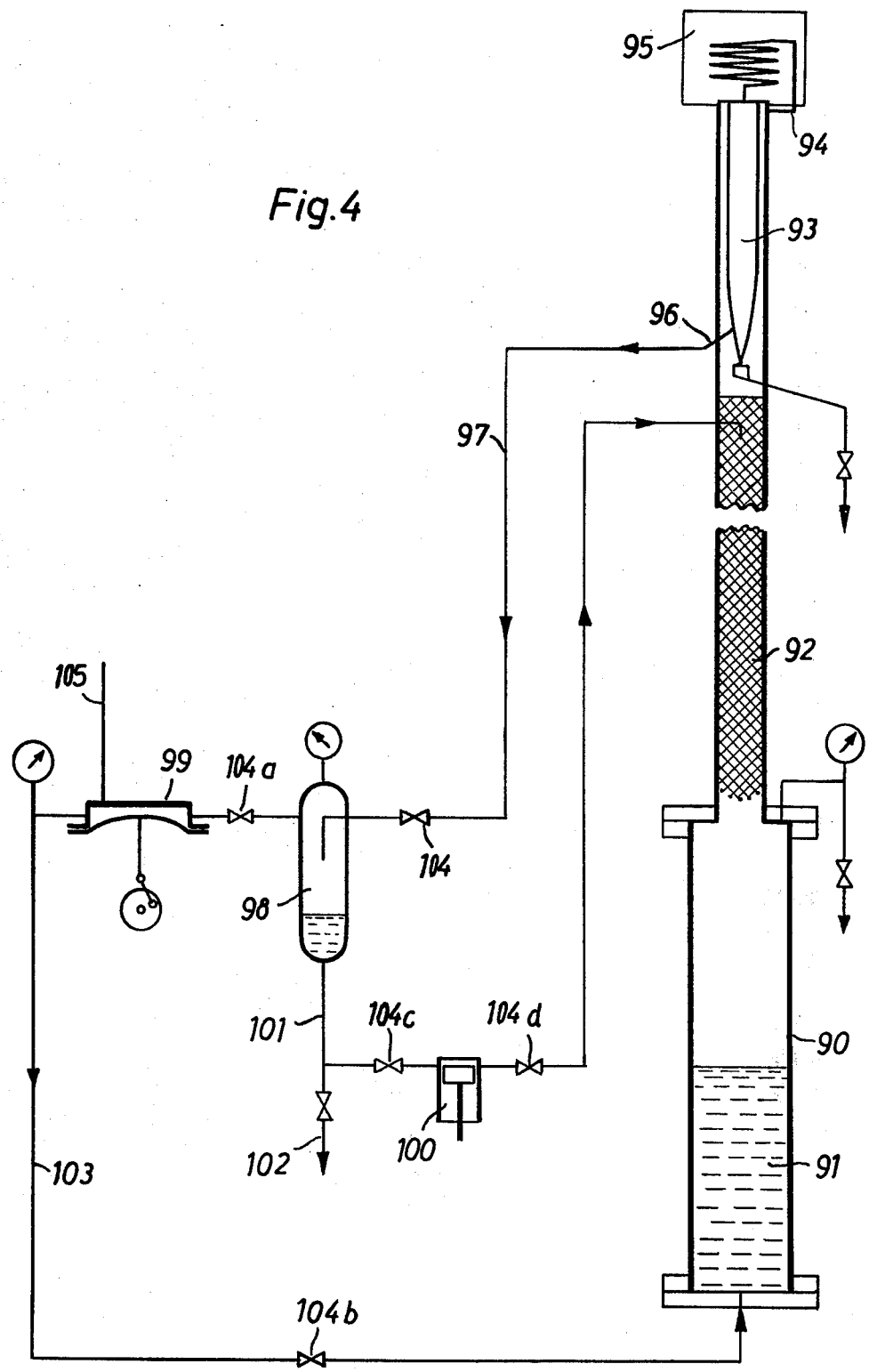

Another method of separating mixtures by the process of the invention is represented in FIG. 4. It has been shown above in the general description that a process which may be particularly advantageous for the separation of a mixture of substances is one where an inert gas stream loaded with a mixture is contacted, in an interchange zone and under supercritical conditions for the inert gas, with the material which has been released from the inert gas after the passage through said interchange zone. It was described above that this is a unit operation which is very similar to fractional distillation as regards the setup and the result of the process. A specific embodiment of the process carried out in accordance with this principle is diagrammatically shown in FIG. 4.

A given amount of a mixture 91 to be separated is contained in the stock vessel 90. An interchange zone 92 which, in the case shown, has the form of a packed column is provided at the top of the stock vessel. At the top of this packed column there is provided a finger-shaped hollow separator 93, the inner space of which communicates with the surrounding space via line 94. Line 94 is passed through a heater 95 by means of which the gas stream flowing through line 94 can be heated. An outlet 96 is provided at the lower end of the finger 93 and permits withdrawal of the gas stream from the interior of this finger. The gas stream is passed through line 97 to the depressurization unit 98 which is connected on one end with the compressor 99 and, at the other end, with the pump 100. The latter connection is realized by line 101 which is provided with an outlet valve 102. The gas stream withdrawn from the depressurization unit 98 is passed, by means of compressor 99, through line 103 and into the base of vessel 90 and thus through the mixture 91 to be separated. 104 to 104d are valves. The temperature of the mixture 91 is maintained in a range above the critical temperature of the circulating inert gas. The compressor 99 forces the inert gas from below through this mixture which is preferably liquid, which results in take-up of part of this liquid in the gas taking also place above the critical pressure. This loaded gas stream passes through the interchange zone 92 and thereafter contacts the finger 93 contructed of a material of high thermal conductivity. A considerable portion of the mixture entrained by the inert gas stream is released therefrom at the surface of this finger. The inert gas stream, as described above, is passed through line 94 and through the heater 95 and thence into the interior of the finger 93. In the heater 95, the inert gas stream is heated up. It then heats the wall of this finger as it passes through the interior of the latter. Thus, the inert gas stream leaving the column 92 contacts the hot wall of the finger 93, is heated up thereby and releases a considerable portion of the entrained compounds which, in normal cases, drop back onto the top of the column 92. If desired and as represented in the drawing, part of this condensate may be withdrawn. Due to the heat exchange between the inflowing and outflowing inert gas stream, merely a minor amount of heat must be supplied at 95 once the process is in full operation.

The inert gas stream which is substantially freed from entrained material is passed through the outlet 96 and into the depressurization unit 98 where the residual portions of entrained compound are released by depressurization. These portions are collected at the bottom of this separator from whence they may either be withdrawn through valve 102 as the product of the separation process or at least partially returned by means of pump 100 to the top of column 92. Returning of the total amount of this material is recommended when the process is started up until equilibrium has been established in the system. Following this, at most a fraction of the product released in 98 is returned. The remainder represents the separated product of the process. The gas stream freed from this product is passed through the compressor 99 and introduced into the base of the vessel 90. Make-up gas can be fed to the system through 105.

When treating a mixture of substances in this manner, it is possible to recover from 98 successively the compounds of the mixture 91 being separated. This is similar to fractional distillation where fractions of different boiling points are obtained in succession. It is to be understood, of course, that, in addition to the measures described herein, a difference as compared with conventional distillation is to be considered. This is the fact that the occurrence of different fractions in distillation operations can be established in a simple manner by varying the temperature of the vapor arriving at the top of the column. This simple visual means of determining the beginning and the end of a fraction does not exist in case of the process of the invention, it being rather necessary to supervise the chemical composition of the loaded inert gas stream withdrawn through 97 or of the separated product released in 98 to determine the occurrence of new fractions of separated products. To this end, any of the great number of determination methods which have been developed in chemical analytics and technology can be used in the process of the invention. Thus, the result of the separation process can be easily monitored by continuously analysing the compounds issuing from the column or by examining specific physical properties of the issuing loaded inert gas stream. Since these are measures known per se, detailed discussion thereof is unnecessary.

The interchange of the loaded inert gas stream with the recirculated separated product in column 92 is essential for the performance of such a separation operation which is similar to distillation. The manner in which this interchange is ensured is left to the particular technological need. It is to be understood that the combination of temperature increase and depressurization may be replaced by only one of these release methods within or outside the interchange column. If the release is effected outside the column, care must be taken for sufficient reflux in the column by returning part of the product separated.

Figure 5:
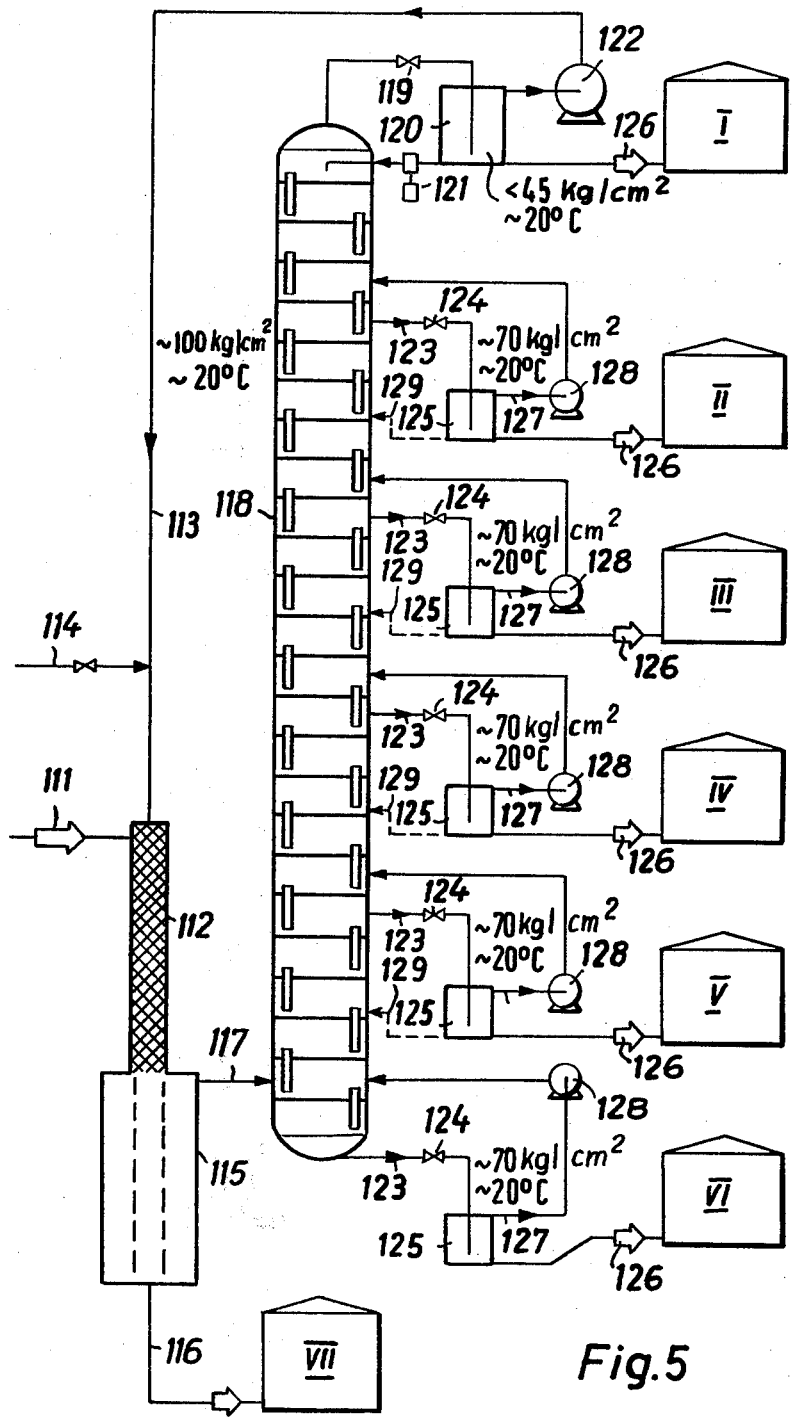
Figure 6:
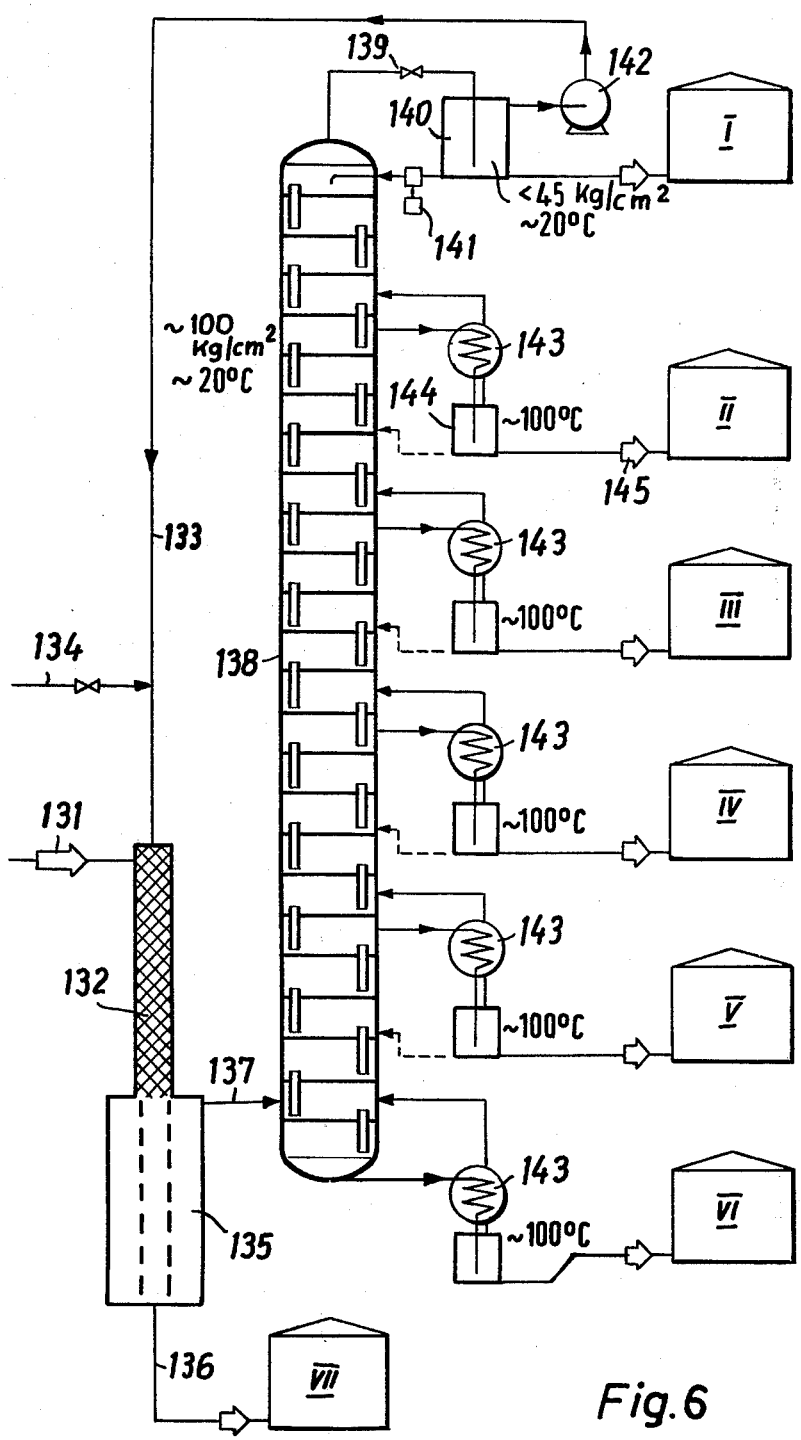

A further development of such a fractional separation on the basis of the new principle is illustrated in FIGS. 5 and 6. The apparatus shown in FIG. 4 operates batchwise. In contrast, the units diagrammatically shown in FIGS. 5 and 6 operate continuously.

These Figures are explained hereafter in connection with an example relating to the continuous separation of a mixture of hydrocarbon compounds, e.g. crude oil or petroleum fractions, by means of ethylene as the supercritical separating gas. It is stressed again that this description is merely given by way of example and does not restrict the principle of general applicability of the process of the invention.

The starting material, e.g. the hydrocarbon fraction, is passed through line 111 and into a saturator 112 to which is also connected the gas recycling line 113 through which recycled supercritical gas is returned for reuse after having been freed from portions of the mixture being separated which have previously been taken up. Any make-up gas which may be required may be fed to the saturator through line 114. In this saturator, the inert gas takes up under supercritical conditions of temperature and pressure those portions of the mixture being separated which are not sufficiently difficultly absorbable under the operating conditions to be withdrawn as residue VII through the separator 115 and line 116. The loaded supercritical gas is continuously passed through line 117 and into the interchange zone 118 which is diagrammatically shown as a tray column. The inert gas is allowed to flow in upward direction through the column 118. Those portions of the mixture of substances taken up which are still contained in the gas are released therefrom, e.g. by depressurization to below the critical pressure, by means of the relief valve 119 and pass into receiver 120 from which at least part of the released liquid is returned to the top of column 118 by means of the reflux pump 121 thereby ensuring the presence of the liquid phase in this interchange zone. The inert gas freed from compounds taken up is again brought to the initial supercritical pressure by means of the recycle and compression pump 122 and returned into the saturator 112 through line 113.

Points of withdrawal 123 are provided laterally at the column through which portions of the loaded supercritical inert gas can be withdrawn from the gas phase present on the particular plate. The relief valves 124 permit partial depressurization which has the result that part of the compounds contained in the inert gas and withdrawn through 123 is released and passed into the associated receiver 125. The separated products desired can be withdrawn from these receivers 125 and the receiver 120 provided at the top of the column through lines 126. The supercritical gas phase which has been freed only partially from material taken up by this partial depressurization is passed through lines 127 and compression pumps 128 into the separation column 118 together with the remainder of the compounds taken up by the gas phase. As may be seen from FIG. 5, recirculation of the gas through lines 127 and subsequent introduction into column 118 are always effected at a point located above the withdrawal of the side streams. It is not necessary, of course, that lines 127 are returned to the next upper plate, it being also possible that several plates lie between 123 and 127.

To illustrate the operation described in this example, the pressures and temperatures used are indicated in FIG. 5. As may be seen, all of the process steps are operated at about the same temperature of 20°C. Merely ingenious gradation of the pressure within the individual separation steps is necessary to obtain the result desired. In the interchange column 118, the reference pressure of 100 kgs./sq.cm. has been selected. For partial depressurization, the reduced value of 70 kgs./sq.cm. is shown within this example, and the lower pressure of 45 kgs./sq.cm. is shown for complete release of the absorbed compounds from the gas in the relief valve 119 and the associated receiver 120 by depressurization to below the critical pressure.

It is within the scope of the invention that not only the pressure is varied but that instead or simultaneously the temperature in the different process steps is adapted to the particular optimum conditions. Before discussing in detail this variation with reference to FIG. 6, the importance of the result of the separation effected with the apparatus shown in FIG. 5 is briefly illustrated. The products obtained by the separation are the fractions I to VII. The fraction which is most difficultly taken up is the residue VII while fraction I is that which is most readily taken up. The intermediate fractions decrease in absorbability by the supercritical gas under the process conditions in the order from I to VII. If absorbability and volatility parallel each other as it is very frequently the case, these fractions decrease in volatility from I to VII or, conversely, they increase in volatility in the direction to the fraction withdrawn at the top of the column as compared with that withdrawn at its base.

A corresponding example is represented schematically in FIG. 6. The overall apparatus is not substantially different from that shown in FIG. 5. However, the relief valves 124 are replaced by heaters 143 which, for example, may be heat exchangers and by means of which the partial gas streams withdrawn through lines 123 (which are not provided with reference numbers in FIG. 6) may be heated. Thus, in this case, partial release of the fractions desired as the product of the separation process is effected by heating the side streams 123. As shown by way of example in FIG. 6, the column 138 is operated at a temperature of about 20°C. while the second separation steps are maintained at temperatures of about 100°C. The only exception in this case is complete release of the portions taken up from the overhead product, this release being also effected by depressurization to below the critical pressure. This is accomplished by means of the relief valve 139 which, as shown in this non-restrictive example, reduces the pressure to 45 kgs./sq.cm. Recycle and compression pump 142 restores the initial pressure of the inert gas stream, i.e. 100 kgs./sq.cm., and then returns the stream through line 133 into the saturator 132. The reflux is returned into the column 138 from the receiver 140 by means of the liquid pump 141. Make-up gas can be added to the cycle through line 134 and the product to be separated is fed through 131. After passage through the saturator, the loaded gas stream is introduced into the column 138 through 137 and that portion of the material fed through 131 which is not taken up leaves the separator 135 through 136 as the residue VII.

As shown in this non-restrictive example represented in FIG. 6, the separation column 138 and the additional separation steps for the side streams of the column are operated under the constant pressure of 100 kgs./sq.cm. Of course, the measures taken in the examples of FIGS. 5 and 6 may be combined by effecting the release of product from the side streams in the additional separation stages by a combination of temperature increase and pressure reduction.

The product fractions I to VII correspond on principle to those of FIG. 5. Of course, they need not be identical with them.

It is also possible when operating the process in the manner represented in FIGS. 5 and 6 to withdraw from the second separation stage not only the supercritical gas phase loaded with the undesirably low residue of the compound and return it into the interchange zone. It is also possible to return part of the product released in the second separation stage into the first separation stage. In this manner, these components of the material can be passed several times through the first separation stage thereby favorably influencing the separation effect. In this case, only part of the product released from the gas in the second separation stage is withdrawn as the desired product from the overall process. Another part is returned into the separation column 118 and 138, respectively. Apart from an improved separation effect, it is also possible, for example, to maintain thereby in a simple manner a sufficient amount of liquid in the particular section of the exchange zone 118 and 138, respectively. FIGS. 5 and 6 show the simple operation of this embodiment of the invention. It is not the total product which is withdrawn from release vessels 125 of FIG. 5 and 144 of FIG. 6 through lines 126 and 145, respectively. Only a partial stream of this product is returned into the column. To this end, line 129 is provided in FIG. 5 and also shown in FIG. 6. As may be seen from this representation, it may be preferred in accordance with the invention to introduce these returned product components into column 118 and 138 at a point which is closer to the point where the loaded supercritical separating gas is introduced (117 and 137) than the point where the associated side stream is withdrawn (e.g. 123 in FIG. 5).

Example 1

The apparatus shown in FIG. 1 is used. The substance to be treated is filled into a 1 liter stirred autoclave standing as needed by the particular temperature in a water or oil bath (not shown) maintaining the autoclave and the substance contained therein at a constant temperature. The gas is introduced through a gas inlet opening in the bottom of the autoclave until the pressure desired is reached. Compressed gas is then withdrawn through the relief valve at the top of the autoclave. The pressure maintained downstream of the relief valve, i.e. in the glass burette connected thereto, is atmospheric. In the glass burette, the substance taken up by the gas in the supercritical state is released from the gas which may escape through the gas meter where it is measured. While compressed gas is withdrawn through the relief valve, sufficient compressed fresh gas is introduced through the opening at the bottom of the autoclave that the pressure in the autoclave is always constant.

In this manner, 250 ml. of paraffin oil are treated with ethylene at a pressure of 200 atmospheres and increasing temperatures above the critical temperature of ethylene. The following result was obtained:

Every 125 grams of ethylene are capable of separating from the paraffin oil

| | |
|---|---|
| at 12°C. | 40 ml. of paraffin oil |
| at 23°C. | 33 ml. of paraffin oil |
| at 50°C. | 15 ml. of paraffin oil |
| at 70°C. | 9 ml. of paraffin oil |

On the other hand, at a constant temperature of 23°C., every 125 gms. of ethylene are capable of taking up in dependence on pressure:

| | |
|---|---|
| at 200 atmospheres | 33 ml. of paraffin oil |
| at 100 atmospheres | 6 ml. of paraffin oil |
| at 50 atmospheres | 0.5 ml. of paraffin oil |

The two series of experiments show that at constant pressures the amount of paraffin oil taken up by ethylene increases as the operating temperature falls toward the critical temperature of ethylene (9.7°C.). When operating at a constant temperature, the amount of paraffin oil taken up increases as the pressure increases.

Example 2

Three different compounds are treated with ethylene in supercritical state under otherwise identical conditions. The following three compounds having the different volatilities indicated are used:

| | |
|---|---|
| Aluminum-sec. butylate, | b.p. about 160°C./1 mm. Hg |
| Paraffin oil, | b.p. about 180°C./1 mm. Hg |
| Silicone oil, | b.p. about 290°C./1 mm. Hg |

Every 125 gms. of ethylene are capable of separating under identical reaction conditions
 46 ml. of aluminum-sec. butylate,
 35 ml. of paraffin oil,
 2.6 ml. of silicone oil.

It is apparent from these three experiments that the amount of the compounds taken up by ethylene under supercritical conditions increases as the volatility of the compound taken up increases even though fundamentally different classes of materials are involved with respect to the chemical formula.

Example 3

Ethylene in amount of 125 g. is capable at 200 atmospheres and different reaction temperatures, but otherwise identical process conditions, to take up the following amounts of aluminum-sec. butylate:
AT 20°C. 46 ml.
At 80°C. 32 ml.

Example 4

A suspension of ammonium chloride in paraffin oil is treated with ethylene in supercritical state (25°C., 200 kgs./sq.cm.). The paraffin oil is taken up as usual. Ammonium chloride cannot be detected in the product obtained after depressurization of the supercritical gas separated. Thus, this inorganic compound was not taken up by the non-polar ethylene in supercritical state.

Example 5

Ethylene is passed at 75°C. and 200 atm through 500 gms. of aluminum alcoholate which had been prepared by oxidation of a growth product prepared from aluminum triethyl and ethylene and having an average carbon number of $C_{12}$ and which had been freed from all separable olefins and by-products by distillation. In this manner, 60 gms. of hydrocarbon by-products can still be separated from the alcoholate. The alcohols obtained after hydrolysis of the alcoholate thus obtained did no longer show any contamination by otherwise usual by-products when analyzed by gas chromatography while considerable amounts of these by-products are detected by gas chromatography in alcohols obtained from the non-purified alcoholate.

Example 6

Sulfuric acid dimethyl ester is treated with an ethylene stream at 23°C. and 200 kgs./sq.cm. 6 ml. of the ester are taken up by 125 gms. of ethylene under these supercritical conditions. Sulfuric acid is not taken up under the same conditions by ethylene maintained under supercritical conditions. Thus, introduction of the organic groups into the purely inorganic compound had the result that the latter could be taken up in supercritical ethylene in accordance with the invention.

Example 7

In the apparatus shown in FIG. 1, 300 ml. of paraffin oil (DAB 6) were treated with ethylene maintained at 200 kgs./sq.cm. and at 20°C. 19 ml. of paraffin oil were separated with 100 liters of ethylene (measured under normal conditions) and collected in the glass burette.

When filling the autoclave with a mixture of 225 ml. of paraffin oil and 75 ml. of dodecene and repeating the experiment under otherwise analogous cponditions, 53 ml. of paraffin oil are obtained in addition to 18 ml. of dodecene.

Example 8

Example 7 is repeated except that ethylene is passed through the autoclave under a pressure of 100 atm. and 75 atm, the autoclave being filled with a mixture of 225 ml. of paraffin oil and 75 ml. of dodecene. At 100 atm, 100 normal liters of ethylene separate 15 ml. of product containing 70% of olefins while the amount separated at 75 atm is only 7.5 ml., the olefin content in the latter case being 90%.

Example 9

Ethylene was passed through 300 ml. of dibutyl ether (b.p., 142°C.) contained in the apparatus shown in FIG. 1, the temperature being 20°C. and the pressure 200 atm. Every 100 gms. of ethylene withdrawn had taken up about 70 ml. of dibutyl ether.

Example 10

In the apparatus shown in FIG. 1, ethylene was passed at 20°C. and 200 kgs./sq.cm. through 300 ml. of methyl ethyl ketone (b.p., 79.5°C.). Every 100 gms. of ethylene withdrawn was loaded with about 50 ml. of substance.

Example 11

In the apparatus of FIG. 1, ethylene maintained at 20°C. and 200 kgs./sq.cm. was passed through 210 ml. of formic acid. Every 100 gms. of ethylene withdrawn was loaded with about 2 ml. of formic acid.

Example 12

In the apparatus of FIG. 1, ethylene was passed at 20°C. and 200 kgs./sq.cm. through 300 ml. of used gear oil (black). Every 100 gms. of ethylene withdrawn was loaded with about 25 ml. of oil which was of light yellow color. More than 90% of the oil could be taken up and released in this manner.

Example 13

In the apparatus of FIG. 1, $CO_2$ was passed at 50°C. and 120 kgs./sq.cm. through a mixture of 250 ml. of paraffin oil and 250 ml. of dodecene. Every 100 normal liters of $CO_2$ removed about 20 ml. of product which comprised 89% of dodecene.

Example 14

In the apparatus of FIG. 1, ethylene was passed at 20°C. and 200 kgs./sq.cm. through 300 ml. of rich milk (3.5% of fat). About 1.3 ml. of fat were removed by 600 normal liters of ethylene.

Example 15

This example illustrates that the transition of the substance to be separated into the supercritical gas phase of the carrier gas and the release of the substance taken up from the gas phase on depressurization do not involve a measurable transformation of energy.

The experiment was again carried out in the apparatus shown in FIG. 1 except that the relief valve was installed in a calorimeter containing about 3 liters of water and could be actuated externally. The autoclave was maintained exactly at 20°C. A thermocouple was provided in the interior of the autoclave to measure the inner temperature. Ethylene was introduced into the empty autoclave until the pressure was 200 kgs./sq.cm. and temperature equalization was allowed to occur. Then compressed ethylene was withdrawn through the relief valve at a rate of 100 normal liters per hour (measured with the gas meter) and depressurized to atmospheric pressure. Similar to all of the previous experiments, the same amount of compressed ethylene of 20°C. was introduced through the opening in the bottom of the autoclave to make up for the amount withdrawn so that the pressure remained at a constant level. Depressurization of 100 normal liters of compressed ethylene was accompanied by a temperature drop of the calorimeter by 2.5°C. when reducing pressure from 200 at to atmospheric,
2.2°C. when reducing pressure from 100 at to atmospheric,
1.0°C. when reducing pressure from 50 at to atmospheric,
0.4°C. when reducing pressure from 30 at to atmospheric, Now 300 ml. of dodecene were added to the autoclave and ethylene was again introduced until the pressure was 200 atm. Compressed ethylene was again withdrawn through the relief valve provided at the calorimeter at a rate of 100 normal liters per hour (measured at the gas meter). Depressurization of 100 normal liters of ethylene from 200 atmospheres to atmospheric pressure was again accompanied by cooling of the calorimeter by 2.5°C. However, in this case 100 normal liters of ethylene had also discharged 73 ml. of dodecene which dropped into the glass burette upon depressurization.

On the other hand it was observed that the temperature in the interior of the autoclave does not change while the compressed ethylene is loaded with dodecene, i.e. neither loading nor release or separation proceed with a transition of energy which is measurable under these conditions.

Example 16

In the apparatus shown in FIG. 1, ethylene was passed through 200 ml. of benzyl alcohol (b.p., 205°C.). at 25°C. and 100 atmospheres. The amount of benzyl alcohol discharged with 125 ml. of ethylene was 1.1 ml.

Example 17

In the apparatus of FIG. 1, ethylene was passed through 200 ml. of 2-ethyl hexanol-(1) (b.p., 183.5°C.) at 25°C. and 100 kgs./cm$^2$. This compound could be discharged in an amount of 26 ml. by 125 gms. of ethylene.

Example 18

In the apparatus of FIG. 1, ethylene was passed through 200 ml. of aniline at 25°C. and 100 kgs./sq.cm. 5 ml. of aniline could be discharged with about 125 gms. of ethylene.

Example 19

In the apparatus of FIG. 1, ethylene was passed through 200 ml. of cyclohexylamine at 25°C. and 115 kgs./sq.cm. The amount of cyclohexylamine discharged by 125 gms. of ethylene was 55 ml.

Example 20

In the apparatus of FIG. 1, ethylene was passed through 200 ml. of cyclohexanol at 20°C. and 100 kgs./sq.cm. The amount of cyclohexanol discharged with 125 gms. of ethylene was about 5 ml.

Example 21

In the apparatus of FIG. 1, ethylene was passed through 200 ml. of pentanediol-(1,5) at 20°C. and 100 kgs. per sq.cm. About 0.3 ml. of this compound were discharged with 125 gms. of ethylene.

Example 22

In the apparatus of FIG. 1, ethylene was passed through 300 ml. of nitrobenzene at 24°C. and 75 atm. About 125 gms. of ethylene discharged 7 ml. of nitrobenzene.

Example 23

In the apparatus of FIG. 1, $N_2O$ was passed through 100 ml. of hexadecene at 40°C. and 100 atm. About 8 ml. of hexadecene were discharged by 100 normal liters of $N_2O$.

Example 24

This experiment is carried out in an apparatus which on principle is similar to that shown in FIG. 1 except that the 1 liter stirred autoclave is replaced by a 200 ml. iron autoclave which is not equipped with a stirrer and the gas meter which contains water is disconnected.

In this autoclave, $NH_3$ is passed through 40 ml. of paraffin oil at 160°C. and 350 atmospheres. The paraffin oil is readily taken up by the ammonia in supercritical state and passes over with the ammonia withdrawn.

Example 25

This experiment is again carried out in an apparatus which on principle is similar to that of FIG. 1 except that the 1 liter stirred autoclave is replaced by a $V_2A$ stainless steel autoclave of 50 ml. capacity. In this autoclave, ethylene at a temperature of 20°C. and under a pressure of 200 atmospheres is passed through 25 gms. of yolk (of fresh hen's eggs). 600 ml. of ethylene withdrawn discharged 0.5 ml. of fat.

Example 26

In the manner described in Example 25, ethylene was passed through 25 gms. of vegetable oil, the temperature being 20°C. and the pressure 200 kgs./sq.cm. 300 liters of ethylene withdrawn discharged 1 ml. of oil.

Example 27

This experiment is carried out in an apparatus which on principle is similar to that of FIG. 1 except that the stirred autoclave is replaced by a 50 ml. autoclave of plexiglass. The autoclave consists of a plexiglass tube of 2 cm. inside diameter and 1.5 cm. wall thickness which is clamped between two iron flanges with gaskets. In the interior of the autoclave, a copper capillary is installed through which water is passed to maintain the inner space at a constant temperature since heat can hardly be supplied and removed through the plexiglass which is of poor thermal conductivity. The use of this autoclave permits direct observation of the processes taking place therein.

Ethylene was passed through a mixture of 8 ml. of anhydrous glycerol and 16 ml. of butanol at a temperature of 20°C. At a pressure of about 30 kgs./sq.cm., the mixture separates into component parts. When the pressure is increased above the critical pressure, the butanol passes into the supercritical gas phase and is discharged with the ethylene withdrawn while the glycerol remains quantitatively in the autoclave.

Example 28

Example 42 is repeated except that ethylene is passed through a mixture of 8 ml. of glycerol and 16 ml. of propanol, the temperature being 20°C. At a pressure of 80 kgs./sq.cm., the mixture is separated into component parts. The propanol is discharged quantitatively by the ethylene while the glycerol again remains in the autoclave.

Example 29

1 kg. of spinach was comminuted with 1 liter of butanol in a high speed mixer ("Starmix"). After centrifuging, a deep green solution of chlorophyll in butanol was obtained. 500 ml. of this solution were mixed with 200 ml. of paraffin oil and the butanol with the water dissolved therein were largely distilled off in vacuo under conditions which were as careful as possible.

Ethylene is passed through 20 ml. of the resultant solution of chlorophyll in paraffin oil, the temperature being 25°C. and the pressure 200 kgs./sq.cm. When introducing ethylene to a pressure of 200 kgs./sq.cm., the volume of the paraffin oil increases by solvation by about 30%. When passing through further amounts of ethylene under 200 kgs./sq.cm., growth in volume of the paraffin oil discontinues. The ethylene passed through rather entrains solvated paraffin oil and also solvated chlorophyll from the liquid phase in the supercritical gas phase. Of course, this results in a descrease in volume of the liquid phase. The gas phase is of faintly green color. 15 ml. of deep green paraffin oil can be discharged with 100 normal liters of ethylene. Thus, the chlorophyll has passed over together with the paraffin oil via the supercritical ethylene phase.

Example 30

The plexiglass autoclave described in Example 27 is charged with 5 gms. of camphor at a temperature of 25°C. When introducing ethylene, the camphor becomes liquid at a pressure of about 25 kgs./cm$^2$.

This example very clearly illustrates the solvation of solid camphor by gaseous ethylene. When continuing the introduction of ethylene to a pressure of 60 kgs./sq.cm., the volume of the camphor which is now liquid continues to increase slightly due to further solvation. When ethylene is further passed through the solvated camphor under a pressure of 60 kgs./sq.cm., the supercritical ethylene entrains solvated camphor, apparently in molecular distribution, into the supercritical gas phase. When depressurizing the loaded supercritical ethylene, the camphor undergoes desolvation and drops like snow into the burette connected to the relief valve. All of the camphor could be passed over with about 300 liters of ethylene.

Example 31

In the manner described in Example 30, the plexiglass autoclave is charged with 5 gms. of naphthalene and 1 gm. of methylene blue. Ethylene is forced into the autoclave. Temperature, 25°C.; pressure, 65 kgs./sq.cm. The naphthalene does not become liquid at this pressure. However, naphthalene which obviously is only solvated at the surface of the crystals initially is entrained into the supercritical gas phase. When depressurizing loaded ethylene withdrawn, the naphthalene is released like snow in the gas burette. Methylene blue was not taken up in the supercritical ethylene phase. Thus, it is possible in this manner to separate solid naphthalene quantitatively from solid methylene via the supercritical gas phase of a carrier gas.

Example 32

In the manner described in Example 30, 3 gms. of naphthalene and 3 gms. of anthracene are charged to the plexiglass autoclave and ethylene is forced into the latter. Temperature, 25°C.; pressure, 60 kgs./sq.cm. Initially, rather pure naphthalene was released from the ethylene withdrawn and depressurized. After about half of the mixture was dischaged, the pressure was increased to 140 kgs./sq.cm. The product discharged at last was substantially pure anthracene.

Example 33

A mixture of alpha olefins comprising 2 liters of each of the olefins $C_{16}H_{32}$, $C_{18}H_{36}$, $C_{20}H_{40}$, $C_{22}H_{44}$, $C_{24}H_{48}$, and $C_{26}H_{52}$, was separated in the apparatus shown in FIG. 4 using ethane as the separating gas.

The operating temperature in 90 and 92 is 40°C. The heater 95 heats the inert gas stream in line 94 to 120°C. In line 97, the inert gas stream is depressurized via the relief valve 104 to about 40 kgs./sq.cm. and passed to the release unit 98.

The separation is initially carried out under an inert gas pressure of about 60 kgs./sq.cm. which is increased in steps to 160 kgs./sq.cm. as the separation proceeds. The make-up gas required is fed at the compressor unit 99 through line 105. This increase in pressure during the separation has the result that the output of the separation unit remains at about a constant level. This increase in pressure is identical to some extent to the increase in temperature of the bottoms in classical distillation.

After equilibrium has been established in the separation unit, all of the material separated and obtained in 98 is withdrawn through 102. The pure olefins $C_{16}H_{32}$ to $C_{26}H_{52}$ are obtained as main fractions in an amount of 1.5 liters each. Similar to fractional distillation, intermediate fractions of about 0.5 liters each are obtained between the main fractions. Exactly as in case of distillation, the volume of these intermediate fractions is due to the hold-up of the separation unit. The purity of the individual main fractions was 95 to 99% as determined by gas chromatography.

Example 74

In an apparatus identical with that used in Example 33, the mixtures of substances referred to hereafter as Examples 34 to 59 were subjected to the new separation process under the conditions also indicated in the table.

| Example | Inert gas | Operating pressure kgs./sq.cm. | Operating temp. °C. | Mixture of substances separated | |
|---|---|---|---|---|---|
| 34 | Ethylene | 60 | 25 | n-Dodecane | n-tetradecane |
| 35 | " | 60 | 25 | 5-Methyl undecane | 7-methyl-pentadecane |
| 36 | " | 80 | 35 | n-hexadecane | n-eicosane |
| 37 | " | 75 | 30 | n-Hexadecene-(1) | n-octadecene-(1) |
| 38 | " | 90 | 20 | 2-Hexyl-decene-(1) [dimeric octene(1)] | 1-octyl-dodecene-(1) [dimeric decene-(1)] |

-continued

| Example | Inert gas | Operating pressure kgs./sq.cm. | Operating temp. °C. | Mixture of substances separated | | |
|---|---|---|---|---|---|---|
| 39 | " | 85 | 22 | 2-Hexyl-decene(1) | n-eicosane | |
| 40 | " | 110 | 25 | 1-phenyldecane | 1-phenyltetradecane | |
| 41 | " | 140 | 25 | Octanol-(1) | Decanol-(1) | Dodecanol-(1) |
| 42 | " | 65 | 25 | 2-Ethyl-hexanol-(1) | Benzyl alcohol | |
| 43 | " | 110 | 18 | n-Octyl acetate | n-Dodecyl acetate | n-Hexadecyl acetate |
| 44 | " | 110 | 25 | n-Octyl acetate | n-Dodecyl butyrate | |
| 45 | " | 100 | 35 | Octanone-(3) | Decanone-(2) | |
| 46 | " | 85 | 25 | Di-n-butyl ether | Diphenyl ether | |
| 47 | " | 65 | 25 | Cyclohexylamine | Aniline | |
| 48 | " | 75 | 25 | Nitrobenzene | 3-Nitro-o-xylene | |
| 49 | Ethane | 90 | 40 | n-Hexadecane | n-Eicosane | |
| 50 | " | 80 | 40 | n-Tetradecane | n-Octadecane | |
| 51 | " | 70 | 45 | 2-Ethyl-hexanol-(1) | Benzyl alcohol | |
| 52 | " | 100 | 45 | n-Octanol-(1) | n-Decanol-(1) | n-Dodecanol-(1) |
| 53 | " | 65 | 40 | n-Dodecene-(1) Hexadecene-(1) | n-Tetradecene-(1) Paraffin oil | |
| 54 | " | 85 | 40 | Di-n-butyl ether | Paraffin oil | |
| 55 | Carbon dioxide | 120 | 50 | Dodecene-(1) | Tetradecene-(1) | Hexadecene-(1) |
| 56 | " | 90 | 40 | 2-Ethyl-hexanol-(1) | Benzyl alcohol | |
| 57 | Nitrous oxide | 100 | 45 | Tetradecene-(1) | Hexadecene-(1) | Octadecene-(1) |
| 58 | Propylene | 125 | 110 | Hexadecene-(1) | Octadecene-(1) | Eicosene-(1) |
| 59 | Propane | 125 | 110 | Hexadecene-(1) | Octadecene-(1) | Eicosene-(1) |

Example 60

The influence which is exerted by hydroxyl groups in compounds having a plurality of hydroxyl groups and which, as described in the specification, may be an additional barrier to absorption of these compounds in certain supercritical gases is illustrated by a number of the following examples.

Ethylene is passed through 200 ml. of ethylene glycol contained in the apparatus shown in FIG. 1. The operating temperature is 20°C. and the pressure 100 kgs./sq.cm. The ethylene withdrawn does not entrain ethylene glycol. When substituting 1,3-butanediol for ethylene glycol (b.p. of 1,3-butanediol, 204°C.), some although little of the organic compound is taken up in the supercritical gas phase. At 20°C. and 200 kgs./sq.cm., 100 gms. of ethylene withdrawn discharge about 0.5 ml. of 1,3-butanediol.

Example 61

A comparable phenomenon can be observed even with aqueous solutions of monofunctional alcohols.

Ethylene is passed through a mixture of 300 ml. of water and 300 ml. of ethanol contained in the apparatus shown in FIG. 1, the temperature being 20°C. and the pressure 200 kgs./cm.sq. The ethylene withdrawn did not take up ethanol which has been retained by the water wherein it is dissolved. The situation is the same if methanol is substituted for ethanol under the same conditions and with the same relative proportions.

If a mixture comprising water and propanol in the same relative proportions is treated under exactly the same operating conditions, 100 gms. of ethylene withdrawn discharge as much as 70 ml. of 90% propanol as determined by hydrometer. If a corresponding mixture of water and butanol is treated under the same conditions, 100 gms. of ethylene withdrawn discharge about 106 ml. of butanol. The significance of the hydroxyl group in proportion to the hydrocarbon radical of the compound is clearly obvious in this case. If the hydrocarbon radical where solvation with the molecules of the supercritical gas phase is initiated is not very large, the linkage force of the hydroxyl group to adjacent molecules predominates and the compound is not taken up in the supercritical gas phase. However, if the hydrocarbon radical becomes greater, this solvation effect outweighs the additional hindrances derived from the present hydroxyl group and the compounds are taken up in the supercritical gas phase.

This additional hindrance to being taken up in the supercritical gas phase cannot only be attributed to hydroxyl groups. A corresponding phenomenon is also observed if a 1:1 mixture of acetone and water is treated with supercritical ethylene at 20°C. and 170 kgs./sq.cm. Here again, acetone is not discharged by the ethylene.

Example 62

A comparable phenomenon is also apparent from the following experiments:

In the apparatus shown in FIG. 1, ethylene is passed through 300 ml. of cutting oil at 20°C. and 130 kgs./sq.cm. 100 gms. of ethylene withdrawn entrain 25 ml. of the cutting oil. In contrast, if the cutting oil is mixed with the same amount of water and the mixture is treated under substantially the same conditions (20°C., 120 kgs./sq.cm.), the amount of oil entrained by 100 gms. of ethylene withdrawn is only 0.2 ml. Thus, the cutting oil which is emulsified in water is largely retained by the water in this form. If a mixture of 10 parts of water and 1 part of cutting oil is substituted for the 1:1 mixture of water and cutting oil and treated at 20°C. and 160 kgs./sq.cm., less than 0.1 ml. of oil is entrained by 100 gms. of ethylene withdrawn.

Example 63

Ethylene is passed through 300 ml. of anhydrous glycerol contained in the apparatus shown in FIG. 1 at 20°C. and a pressure of 200 kgs./sq.cm. Here again, the inhibiting action of the hydroxyl groups of the glycerol predominates. The ethylene withdrawn does not entrain glycerol. The same phenomenon is apparent if the ethylene is replaced by supercritical propane at a temperature of 120°C. and a pressure of 200 kgs./sq.cm. Here again, glycerol is not entrained by the supercritical propane.

If NH$_3$ is used as the supercritical gas phase in place of the supercritical hydrocarbon gases and the treatment is effected at a temperature of 170°C. and a pressure of 350 kgs./sq.cm., the glycerol, analogously to any other organic compound in normal cases, is readily taken up by the supercritical NH₃ gas phase and can be discharged quantitatively from the pressure vessel with the NH₃ withdrawn. Thus, glycerol passes into the supercritical gas phase of the polar gas without any difficulty while it is not taken up in the supercritical gas phase of the unpolar hydrocarbon compounds.

Example 64

Example 5 describes a process where ethylene under supercritical conditions is passed through aluminum alcoholate contaminated with hydrocarbon compounds. It is described in this example that considerable amounts of hydrocarbon by-products are separated from the alcoholate in this manner while the aluminum alcoholate is not taken up by the supercritical ethylene.

If the aluminum alcoholate after this purification is again treated with a supercritical gas phase in accordance with the invention using NH₃ as the supercritical gas at 170°C. and 350 atmospheres, this aluminum alcoholate is readily taken up in the supercritical NH₃ stream and can be discharged from the apparatus quantitatively. Here again, it becomes apparent that disturbances encountered when transferring compounds containing organic groups into the supercritical gas phase can be eliminated by selection of the suitable supercritical gas if these disturbances are attributable to additional linkage effects of specific groups of the compounds to be taken up.

Example 65

Pure heptene is placed into the pressure apparatus shown in FIG. 1. Ethylene at a temperature of 25°C. is introduced from below into the pressure vessel of plexiglass which is initially closed. In introducing the ethylene, the volume of the liquid heptene undergoes an unlimited growth due to solvation of the heptene with ethylene until the entire autoclave is occupied by the solvated heptene at about 60 kgs./sq.cm. Separation of an ethylene stream from the solvated heptene is impossible. Formation of a solvated liquid phase in addition to a supercritical gas phase separated therefrom does not take place. This is a typical example of the interference effect which may exhibited by some compounds, particularly compounds of high volatility.

If, however, a less volatile compound which can be homogeneously mixed with heptene, e.g. paraffin oil, is added to the heptene in a ratio of 1:1, some increase in volume by solvation will still occur when forcing ethylene into the pressure vessel, but this increase is only of a limited extent and it is possible after a short time to separate an ethylene gas stream loaded with heptene from the liquid phase under supercritical conditions. Of course, the paraffin oil will also pass into the supercritical gas phase to an increasing extent during this treatment.

Example 66

A stream of CF₃Cl is passed at 42°C. and 70 kgs./sq.cm. through 20 ml. of paraffin oil contained in a 50 ml. pressure vessel of plexiglass. The increase in volume of the paraffin oil occurring thereby is hardly noticeable. The supercritical gas withdrawn discharges paraffin oil, the amount of which is low, however, corresponding to the low degree of solvation. When increasing the pressure to about 75 kgs./sq.cm., the density of the supercritical gas phase is higher than that of the paraffin oil. This has the result that the paraffin oil migrates to the top of the pressure vessel while the supercritical gaseous trifluorochloromethane is present below it at the bottom. Thus, continuous treatment of the paraffin oil with the supercritical gas requires reversal of the direction of flow of the supercritical gas stream. This example shows that even reversal of the relative densities between the inert gas phase and the mixture of substances to be separated can be achieved by selecting appropriate process conditions.

Example 67

Crude oil is subjected to a continuous separation process in the apparatus shown in FIG. 2. The process is operated with ethylene as the supercritical gas at a temperature of 20°C. The pressure in the mixer 31 and in the pressure separator 32 is maintained at 120 kgs./cm.sq. The pressures in the pressure separators 33 to 36 downstream thereof decrease in steps and are 110 kgs./sq.cm. in pressure separator 33; 95 kgs./sq.cm. in pressure separator 34; 70 kgs./sq.cm. in pressure separator 35, and 40 kgs./sq.cm. in pressure separator 36. Four fractions totalling more than 50% by weight of the crude oil are released in the pressure separators 33 to 36 in addition to the residue which has not been taken up under the conditions described above and which has been recovered from pressure separator 32. The composition of the fractions is as follows:

| Fraction | Boiling point up to 125°C./ 18 mm. Hg | Boiling point 30 – 125°C./ 0.5 mm. Hg | Boiling point above 124°C./ 0.5 mm. Hg |
|---|---|---|---|
| 1 | 85 | 15 | — |
| 2 | 32 | 43 | 25 |
| 3 | 23 | 35 | 42 |
| 4 | 17 | 25 | 58 |

Example 68

Crude oil is subjected to continuous separation in the apparatus shown in FIG. 3. Stepwise release of the petroleum fractions is effected by stepwise increase in the temperature in pressure separators 62–66. The temperatures maintained are 20°C. in the mixer 61 and in pressure separator 62; 50°C. in pressure separator 63; 80°C. in pressure separator 64; 110°C. in pressure separator 65, and 140°C. in pressure separator 66. The petroleum residue which has not been taken up is withdrawn via 72. By means of the pressure separators 63–66 and the associated take-off means 75–78, separation of the mixture taken up into the following four fractions is accomplished:

| Fraction | Boiling range up to 125°C./ 18 mm. Hg | Boiling range 30 to 125°C./ 0.5 mm. Hg | Boiling range above 124°C./ 0.5 mm. Hg |
|---|---|---|---|
| 1 | 80 | 20 | — |
| 2 | 42 | 38 | 20 |
| 3 | 25 | 30 | 45 |
| 4 | 16 | 27 | 57 |

Several examples are listed hereafter of the great numer of organic compounds which can be subjected to the process of the invention to illustrate still further the great variety of compounds which can be used in this process. The enumeration of these few specific compounds is not intended to restrict the new separation process thereto. These compounds are rather to be understood as typical examples which are representative of the respective groups and classes of compounds.

Normal paraffins such as decane, undecane, dodecane, undecane, tridecane, tetradecane, pentadecane, hexadecane, heptadecane, octadecane, nonadecane, eicosane . . . . , pentacosane . . . , triacontane, etc.

Isoparaffins such as 2,3-dimethyloctane, 3-methylundecane, 5-n-butyl-nonane, 6-n-propyl-dodecane, 7,8-dimethyltetradecane, 4,9-di-n-propyl-dodecane, 2,6,11,15-tetramethyl-hexadecane.

n-Olefins such as decene-(1), undecene-(1), dodecene-(1), dodecene-(6), tridecene-(1), tetradecene-(1), pentadecene-(1) . . . . , eicosene-(1), etc.

Isoolefins such as 2-ethyl-hexene-(1), 2,6-dimethylheptene-(2), 4-n-propyl-heptene-(3), 3-n-butyl-octene-(1), 2-methyltridecene-(1), 2-n-hexyl-decene-(1), 2-decyl-dodecene-(1), 2-n-octyl-dodecene-(1).

Dienes and polyenes such as octadiene-(2,6), 2,5-dimethylhexadiene-(1,5), eicosadiene-(1,19), β-linaloolene, ocimene, myrene, dihydrofarnesane.

Acetylenes such as octyne-(1), octyne-(4), decyne-(1), hexadecyne-(1), octadecyne-(1), octadecyne-(2).

Cycloparaffins, cycloalkanes, cycloalkenes such as n-butylcyclohexane, cyclododecane, cyclodecadiene, cyclododecatriene.

Aromatics such as xylenes, ethyl benzene, propyl benzene, isopropyl benzene, 1,3,5-trimethyl benzene, n-butyl benzene, p-cymene, 1,2-diethyl benzene, prehnitene, 1-phenyl-hexane, 1,3-dimethyl-5-tert.butyl-benzene, 1,4-diisopropyl benzene, 3-phenyl-3-ethyl pentane, 1-phenyl-dodecane; styrene, β-methylstyrene, p-ethylstyrene, 1-phenyl-butene-(1); diphenyl, 4-methyldiphenyl, diphenyl methane, 1,2-diphenyl-ethane, 2,3-diphenyl-butane; 1,1-diphenylethylene, indane, indene, acenaphthene, anthracene, phenanthrene, naphthalene, 1-n-butyl-naphthalene, 2-tert.butylnaphthalene, tetraline, decaline, azulene.

Alcohols such as tert. amyl alcohol, hexanol-(1), heptanol(1), octanol-(1), octanol-(2), 2-ethyl-hexanol-(1), nonalol-(1) . . . . , dodecanol-(1) . . . , hexadecanol-(1), stearyl alcohol, benzyl alcohol, phenyl ethyl alcohol, cinnamic alcohol, cyclohexanol, menthol, terpineol, geraniol, n-amyl-mercaptan, n-hexyl-mercaptan.

Aldehydes such as caproaldehyde, enanthaldehyde, caprylaldehyde, pelargonic aldehyde, capric aldehyde, lauryl aldehyde, sorbic aldehyde, citronellal, oleyl aldehyde, benzaldehyde, salicyl aldehyde, anisaldehyde, nitrobenzaldehyde, vanillin, chlorobenzaldehyde.

Ketones such as methyl-n-butyl-ketone, methyl-n-amyl-ketone, ethyl-n-butyl-ketone, di-n-propyl-ketone, methyl-n-hexyl-ketone, propyl-n-butyl-ketone, methyl-n-heptylketone, methyl-n-decyl-ketone, acetophenone, benzophenone, camphor.

Acids such as formic acid, acetic acid, propionic acid, butyric acid, isobutyric acid, valeric acid, isovaleric acid, methyl-ethyl-acetic acid, pivalic acid, n-caproic acid, tert. butyl-acetic acid, diethylacetic acid, caprylic acid, 2-ethyl-hexanoic acid, capric acid, lauric acid . . . , palmitic acid, stearic acid, valeric acid, valeric acid nitril, oleic acid, benzyl chloride, benzoic acid, salicylic acid, cinnamic acid, nitrobenzoic acid.

Esters such as n-amyl formiate, n-octyl-formate, benzyl formate, n-butyl acetate, isobutyl acetate, n-hexylacetate, 2-ethylbutyl-acetate, n-octyl acetate, n-decyl acetate . . . , n-octadecyl acetate, phenyl acetate, benzyl acetate, β-phenylethyl acetate, glycol-di-acetate, oleyl acetate, n-butyl-propionate, isopropyl butyrate, n-butyl-isobutyrate, n-propyl-valerate, ethyl caprylate, ethyl capric acid ester, benzoic acid methyl ester, dimethyl sulfate, diethyl sulfate.

Halohydrocarbons such as 1-chloro-octane, 2-chlorooctane, 1-chlorodecane, 1-bromohexane, 1-bromooctane, chlorobenzene, dichlorobenzene, bromobenzene, chlorotoluene.

Amino compounds such as primary n-hexylamine, primary n-octylamine, primary n-decylamine, cyclohexylamine, benzylamine, aniline, dimethylaniline, diphenylamine, toluidine.

Ethers such as di-n-propyl ether, di-n-butyl ether, di-isobutyl ether, di-isoamyl ether, ethyl-hexyl ether, anisol, phenetol, diphenyl ether, β-naphthol methyl ether, di-n-propyl sulfide.

Phenol, cresols, xylenols, carvacrol.

What is claimed is:

1. The process of separating a mixture which is in liquid state or solid state or liquid and solid state composed of a plurality of compounds at least one of which contains an organic group which comprises:
    a. contacting said mixture with a gas phase preferentially taking up said compound containing an organic group at the contacting conditions, said gas phase during said contacting being maintained under supercritical conditions of temperature and pressure such that the gas takes up at least a portion of said compound containing an organic group, the temperature being in a range in which the quantity of said compound containing an organic group taken up by said gas phase varies inversely with said temperature, and effecting said contacting in a manner so that this occurs, and so that there is a substantial gas component that is identifiable as a gaseous component, the critical temperature of said gas phase being in the range of 0°–200°C, the temperature of said gas phase during said contacting being within about 100°C above the critical temperature,
    b. separating the gas phase in the form of said identifiable gaseous component loaded with said portion of the compound containing an organic group taken up during said contacting from any of the mixture not taken up by the gas phase while still maintaining supercritical conditions as aforesaid,
    c. thereafter separating at least part of the compound containing an organic group taken up, from the gas phase.

2. Process according to claim 1, wherein said contacting is effected by passing the gas phase into contact with said mixture.

3. The process according to claim 2, wherein said mixture contains a plurality of said compounds containing an organic group and a plurality of said compounds containing an organic group are taken up by the gas.

4. The process as claimed in claim 3, which comprises releasing compounds taken up in the supercritical gas phase, contacting at least part of the released material with the loaded gas stream in an interchange zone under supercritical conditions for the gas phase used, for the rectification of the loaded gas.

5. The process according to claim 4, wherein product of the separation process is taken from the interchange zone.

6. The process according to claim 4, wherein product of the separation process is separated from gas stream from said interchange zone.

7. The process as claimed in claim 4, wherein the loaded gas stream and said released material are passed through said interchange zone countercurrently.

8. The process as claimed in claim 4, which comprises effecting said releasing by raising the temperature of the supercritical gas phase, releasing from the gas stream which has been freed from compounds taken up, in a separate process step and by depressurization, further portions of the compounds taken up, recovering at least part of these compounds as product of the separation process, and returning said gas stream, after sufficient re-compression, to be loaded with further amounts of the compounds to be separated.

9. The process as claimed in claim 8, wherein part of the material obtained by said depressurization is introduced into the interchange zone for use in the rectification.

10. The process as claimed in claim 4, wherein said interchange zone is operated at substantially constant pressure and temperature.

11. The process as claimed in claim 4, wherein an additional influence is exerted on the rectification in said interchange zone by varying at least one of the temperature and the pressure.

12. Process according to claim 4, which comprises effecting said releasing by reducing the pressure.

13. The process as claimed in claim 3, wherein a supercritical gas phase loaded with a mixture of substances is subjected to stepwise recovery and the products of these steps are recovered separately.

14. The process of claim 2, wherein said separation in step (c) is caused by raising the temperature, reducing the pressure or raising the temperature and reducing the pressure of the gas phase.

15. The process according to claim 2, wherein the temperature of said gas phase during said contacting is within about 50°C. above the critical temperature.

16. The process according to claim 2, wherein the temperature of said gas phase during said contacting is within about 20°C. above the critical temperature.

17. The process of claim 2, wherein the supercritical gas phase is inert with respect to the mixture under the process conditions.

18. The process of claim 1, wherein said contacting temperature is about 0° to 200°C.

19. The process of claim 1, wherein the gas is carbon dioxide.

20. The process as claimed in claim 1, wherein the absorbability of said compound containing an organic group is improved by simultaneously using in the loading step a compound which is more readily taken up.

21. The process according to claim 1, wherein said gas is hydrocarbon gas or halogenated hydrocarbon gas phase.

22. The process according to claim 1, said gas phase is ethane, propane, butane, ethylene, or propylene.

23. The process according to claim 1, wherein said gas phase is an inorganic gas.

24. The process according to claim 1, wherein said gas phase is carbon dioxide, ammonia, or $N_2O$.

* * * * *

UNITED STATES PATENT AND TRADEMARK OFFICE
CERTIFICATE OF CORRECTION

PATENT NO. : 3,969,196
DATED : July 13, 1976
INVENTOR(S) : Dr. Kurt Zosel

It is certified that error appears in the above—identified patent and that said Letters Patent are hereby corrected as shown below:

Column 17, line 11, insert "exchange" after --phase--.

Signed and Sealed this

Fourth Day of December 1979

[SEAL]

Attest:

SIDNEY A. DIAMOND

Attesting Officer    Commissioner of Patents and Trademarks